(12) United States Patent
McManus et al.

(10) Patent No.: US 7,199,240 B2
(45) Date of Patent: Apr. 3, 2007

(54) REDUCTIVE ALKYLATION OF SATURATED CYCLIC AMINES

(75) Inventors: James W. McManus, Albany, GA (US); Bryan G. Kriel, Albany, GA (US); Michael Stranberg, Albany, GA (US)

(73) Assignee: Merck & Co., Inc., Rahway, NJ (US)

( * ) Notice: Subject to any disclaimer, the term of this patent is extended or adjusted under 35 U.S.C. 154(b) by 418 days.

(21) Appl. No.: 10/726,091

(22) Filed: Dec. 2, 2003

(65) Prior Publication Data
US 2004/0116692 A1 Jun. 17, 2004

Related U.S. Application Data

(60) Provisional application No. 60/432,570, filed on Dec. 11, 2002.

(51) Int. Cl.
*C07D 401/06* (2006.01)
(52) U.S. Cl. ...................................... 544/360
(58) Field of Classification Search ................ 544/360
See application file for complete search history.

(56) References Cited

U.S. PATENT DOCUMENTS

| 5,413,999 | A | 5/1995 | Vacca et al. |
| 5,508,404 | A | 4/1996 | Askin et al. |
| 5,618,937 | A | 4/1997 | Askin et al. |
| 6,642,237 | B1 | 11/2003 | Tata et al. |

FOREIGN PATENT DOCUMENTS

WO    WO 01/38332 A1    5/2001

OTHER PUBLICATIONS

G.W. Gribble et al., "Sodium Borohydride in Carboxylic Acid Media. A Review of the Synthetic Utility of Acyloxyborohydrides", 1985, vol. 17 (4-5), pp. 317-384, Organic Preparations and Procedures Int.
C.F. Nutaltis, "Reacations of Borohydride in Carboxylic Acid Media: a Summary", 1989, vol. 66, pp. 673-675, J. Chemical Education.
A.E. Moormann, "Reductive Amination of Piperidines with Aldehydes Using Borane-Pyridine", 1993, vol. 23, pp. 789-795, Synthetic Communications.
A.F. Abdel-Magid et al., "Reductive Amination of Aldehydes and Ketones with Sodium Triacetoxyborohydride. Studies on Direct and Indirect Reductive Amination Procedures", 1996, vol. 61, pp. 3849-3862, J. Organic Chemistry.
M. Couturier et al., "Palladium and Raney Nickel Catalyzed Methanolic Cleaveage of Stable Borane-Amine Complexes", 2001, vol. 3, pp. 465-467, Organic Letters.

*Primary Examiner*—James O. Wilson
*Assistant Examiner*—Ebenezer Sackey
(74) *Attorney, Agent, or Firm*—Kenneth R. Walton; Valerie J. Camara

(57) ABSTRACT

Saturated cyclic amines (e.g., piperazines and piperidines) are reductively alkylated with an N-containing heteroaryl carbaldehyde using an alkylcarboxylic acid and a borohydride to obtain a product comprising an N-((N-containing heteroaryl)methyl)-substituted cyclic amine and one or more borane complexes thereof, after which the product is treated with a catalytic amount of a Pt or Pd catalyst in the presence of an alcohol to cleave the borane complex(es) and thereby afford the N-((N-containing heteroaryl)methyl)cyclic amine free of borane complex. Saturated cyclic amines are also reductively alkylated by adding an N-containing heteroaryl carbaldehyde and the amine to a tetrahydroborate salt-alkylcarboxylic acid-solvent admixture and aging the resulting reaction mixture to obtain an alkylated product substantially free of borane complex.

18 Claims, No Drawings

REDUCTIVE ALKYLATION OF SATURATED CYCLIC AMINES

This application claims the benefit of U.S. Provisional Application No. 60/432,570, filed Dec. 11, 2002.

FIELD OF THE INVENTION

The present invention is directed to processes for preparing N-((N-containing heteroaryl)methyl)-substituted saturated cyclic amines (e.g., piperazines and piperidines) by the reductive alkylation of the cyclic amine with an N-containing heteroaryl carbaldehyde using a borohydride reducing agent.

BACKGROUND OF THE INVENTION

N-(N-containing heteroaryl)methyl-substituted cyclic amines are useful as intermediates in the preparation of pharmacologically active substances or as pharmacologically active substances per se. U.S. Pat. No. 5,413,999, for example, discloses a wide range of 5-piperazin-1-ylpentaneamide derivatives that are HIV protease inhibitors useful for treating HIV infection and AIDS. Among the derivatives described in U.S. Pat. No. 5,413,999 are compounds having an azaarylmethyl group substituted at the 4-position of the piperazinyl moiety, including indinavir (Compound J in the patent) which is marketed by Merck under the tradename CRIXIVAN®. As another example, WO 01/38332 discloses γ-hydroxy-α-(phenylmethyl)-2-[((fluoroalkyl)amino)carbonyl]-1-piperazinepentanamide derivatives that are potent inhibitors of HIV protease including mutant forms thereof that are resistant to approved products such as indinavir.

The N-heteroarylmethyl-substituted cyclic amines can be obtained by reductive alkylation of the corresponding cyclic amine with the appropriate heteroaryl carbaldehyde precursor. WO 01/38332, for example, discloses the preparation of 4-[(heteroaryl)methyl]-γ-hydroxy-α-(phenylmethyl)-2-[((fluoroalkyl)amino)carbonyl]-1-piperazinepentanamide protease inhibitors by reacting the corresponding heteroaryl carbaldehyde with the γ-hydroxy-α-(phenylmethyl)-2-[((fluoroalkyl)amino)carbonyl]-1-piperazinepentanamide penultimate in the presence of sodium cyanoborohydride or sodium triacetoxyborohydride (see, e.g., Scheme 1 and Example 59). A drawback to the use of the cyanoborohydride or triacetoxyborohydride is their expense, particularly for large scale production. In addition, the cyanoborohydride is relatively toxic. A further example is U.S. Pat. No. 5,618,937, which discloses (see Example 4) the reductive alkylation of 2(S)-tert-butylcarboxamide piperazine with 3-pyridinecarbaldehyde in the presence of titanium tetraisopropoxide and sodium cyanoborohydride to obtain (S)-4-(3-picolyl)-2-tertbutylcarboxamide piperazine, and the subsequent heating of the alkylated piperazine (see Example 5) with the indinavir epoxide intermediate (i.e., [3aS-[3-[2(S*),3(R*)],3aα,8aα]]-3,3a,8,8a-tetrahydro-2,2-dimethyl-3-[3-(2-oxiranyl)-1-oxo-2-(phenylmethyl)propyl]-2H-indeno[1,2-d]oxazole) to give indinavir penultimate, from which the acetonide moiety was removed by treatment with HCl to provide indinavir. Drawbacks of the reductive alkylation reported in US '937 include the use of a relatively expensive and toxic reducing agent (NaBHCN$_3$) and the relatively low yield (40%). Still another example is U.S. Pat. No. 5,508,404, which discloses the preparation of indinavir by reductive alkylation of 3-pyridinecarbaldehyde with indinavir penultimate in the presence of an excess amount of a reducing agent. The preferred reducing agents are sodium triacetoxyborohydride, sodium cyanoborohydride, and formic acid. Formic acid, however, provided a relatively low yield (43% in Example 2). Furthermore, although NaBH(OAc)$_3$ provided a good yield (88% in Example 1), both it and NaBHCN$_3$ are expensive reagents that would be costly to employ at least on a production scale, especially since an excess amount of the reducing agent is required to react with and remove the by-product water by formation of borate and thereby drive the equilibrium of the reaction toward the product side. US '404 also discloses that sodium borohydride can be used as a reducing agent. NaBH$_4$ and similar tetrahydroborate salts are attractive reducing agents, because they can be effective over a wide pH range, and are inexpensive and non-toxic compared to NaBH(OAc)$_3$ and NaBHCN$_3$. However, US '404 does not recognize or address a significant problem posed by the use of NaBH$_4$; i.e., the elimination of the relatively high stability amine-borane complexes that can form by reaction of borohydrides with pyridyl and other N-containing, π-deficient heteroaryls. These π-deficient heteroaryls (pyridyl, quinolinyl, isoquinolinyl, etc.) are heteroaryls that contain a ring nitrogen in an imine-type structure, the ring nitrogen having a lone pair that is not utilized in the aromatic π system. These ring nitrogens thus have a great tendency to react with electrophiles and to rapidly form unusually stable borane complexes. Conventional methods for cleaving these highly stable amine-borane complexes typically employ strong mineral acids, but these methods cannot be used with acid-sensitive compounds such as indinavir and other piperazinepentanamides of similar structure, nor can they be used with other reductively alkylated cyclic amines that contain acid-sensitive groups such as alcohols, ketones, and esters.

There is a need in the art for reductive alkylation processes that can utilize borohydride reducing agents to prepare products having π-deficient, N-containing hetearyl groups wherein the borane complexes formed during the reaction can be effectively cleaved without degradation of the final product or wherein the reaction can be conducted in such as manner as to avoid the formation of borane products altogether.

The following references are of interest as background:

Gribble et al., *Organic Preparations and Procedures Int.* 1985, 17 (4–5): 317–384 is a review of the properties of sodium borohydride in carboxylic acid media and the synthetic utility of acyloxyborohydrides.

Nutaltis, *J. Chem. Ed.* 1989, 66(8): 673–675 provides a summary of the reactions of borohydride in carboxylic acid media.

Moormann, *Synth. Commun.* 1993, 23(6): 789–795 discloses the reductive alkylation of piperidines with aldehydes using a borane-pyridine complex.

Abdel-Magid et al., *J. Org. Chem.* 1996, 61: 3849–3862 describes the reductive amination of various aldehydes and ketones with sodium triacetoxyborohyride. The reference discloses a direct amination procedure in which the amine and the aldehyde or ketone were reacted in the presence of the triacetoxyborohydride to obtain a product without the formation of an intermediate imine or iminium salt. The reference also discloses a stepwise (or indirect) procedure for use with aldehydes and primary amines that gave significant amounts of dialkylation and other side products in the direct procedure. The stepwise procedure involved reacting the aldehyde and amine in a solvent (usually methanol) to provide an aldimine intermediate, and then treating the aldimine-solvent mixture with solid NaBH$_4$.

Couturier et al., *Org. Letters* 2001, 3(3): 465–467 discloses the use of palladium on carbon and Raney nickel to catalyze the methanolysis of certain borane-amine adducts.

SUMMARY OF THE INVENTION

The present invention is directed to improved processes for the reductive alkylation of cyclic amines. The present invention includes a process for preparing a compound of Formula (I):

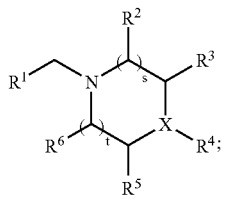

(I)

which comprises:
(A) reacting an aldehyde of Formula (II):

$R^1$—CHO       (II)

with a cyclic amine compound of Formula (III):

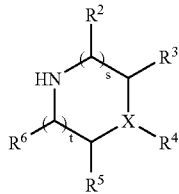

(III)

in an organic solvent and in the presence of a $C_{1-6}$ alkyl-carboxylic acid and with removal of by-product water, to form a reaction mixture comprising an iminium salt of Formula (IV):

$C_{1-6}$ alkyl-COO⁻

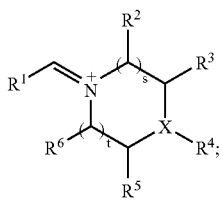

(IV)

(B) adding a tetrahydroborate salt to the reaction mixture of Step A to obtain a product comprising a compound of Formula (I) and one or more borane complexes thereof; and (C) treating the product of Step B with a catalyst selected from the group consisting of Pt oxide, Pt halide, Pd oxide and Pd halide in the presence of an alcohol to cleave the one or more borane complexes and thereby obtain the compound of Formula (I) substantially free of any borane complex thereof;

wherein:
X is CH or N;
$R^1$ is a heteroaryl which is (i) a 5- or 6-membered heteroaromatic ring or (ii) a 9- or 10-membered fused, bicyclic ring system in which both rings are aromatic rings and at least one of the rings is a heteroaromatic ring; wherein the heteroaryl contains at least one carbon atom, one or more nitrogen atoms, optionally one or more O atoms, and optionally one or more S atoms; wherein at least one ring nitrogen in the heteroaryl has an unbonded electron pair that is not utilized in the aromatic π system of the heteroaryl; and wherein the heteroaryl is optionally substituted with from 1 to 5 substituents each of which is independently:
(1) halo,
(2) —$C_{1-6}$ alkyl,
(3) —$C_{1-6}$ alkyl mono-substituted with —OH, —O—$C_{1-6}$ alkyl, —$CO_2R^a$, —S(=O)$R^c$, or —$SO_2R^c$,
(4) —O—$C_{1-6}$ alkyl,
(5) —O—$C_{1-6}$ alkyl mono-substituted with —OH, —O—$C_{1-6}$ alkyl, —$CO_2R^a$, —S(=O)$R^c$, or —$SO_2R^c$,
(6) —OH,
(7) —$CO_2R^a$,
(8) —C(=O)N($R^aR^b$),
(9) —S(=O)$R^c$,
(10) —$SO_2R^c$,
(11) aryl, optionally substituted with from 1 to 5 substituents each of which is independently halo, —OH, —$C_{1-6}$ alkyl, —O—$C_{1-6}$ alkyl, —$CO_2R^a$, —S(=O)$R^c$, or —$SO_2R^c$,
(12) —$C_{1-6}$ alkyl-aryl, wherein the aryl is optionally substituted with from 1 to 5 substituents each of which is independently halo, —OH, —$C_{1-6}$ alkyl, —O—$C_{1-6}$ alkyl, —$CO_2R^a$, —S(=O)$R^c$, or —$SO_2R^c$,
(13) HetA, or
(14) —$C_{1-6}$ alkyl-HetA;
each of $R^2$, $R^3$, $R^5$ and $R^6$ is independently:
(1) —H,
(2) —$C_{1-6}$ alkyl,
(3) —$C_{1-6}$ alkyl mono-substituted with —OH, —O—$C_{1-6}$ alkyl, —$CO_2R^a$, —S(=O)$R^c$, or —$SO_2R^c$,
(4) —O—$C_{1-6}$ alkyl,
(5) —O—$C_{1-6}$ alkyl mono-substituted with —OH, —O—$C_{1-6}$ alkyl, —$CO_2R^a$, —S(=O)$R^c$, or —$SO_2R^c$,
(6) —OH,
(7) —$CO_2R^a$,
(8) —C(=O)N($R^aR^d$),
(9) —S(=O)$R^c$,
(10) —$SO_2R^c$,
(11) aryl, optionally substituted with from 1 to 5 substituents each of which is independently halo, —OH, —$C_{1-6}$ alkyl, —O—$C_{1-6}$ alkyl, —$CO_2R^a$, —S(=O)$R^c$, or —$SO_2R^c$,
(12) —$C_{1-6}$ alkyl-aryl, wherein the aryl is optionally substituted with from 1 to 5 substituents each of which is independently halo, —OH, —$C_{1-6}$ alkyl, —O—$C_{1-6}$ alkyl, —$CO_2R^a$, —S(=O)$R^c$, or —$SO_2R^c$,
(13) HetA, or
(14) —$C_{1-6}$ alkyl-HetA;
$R^4$ is:
(1) —H,
(2) —$C_{1-20}$ alkyl, which is:
(a) optionally substituted with from 1 to 7 substituents each of which is independently:
(i) —OH,
(ii) —$C_{1-6}$ alkyl,
(iii) —O—$C_{1-6}$ alkyl, (iv) —CO$_2$R$^a$,
(v) —C(=O)N(R$^a$R$^b$),
(vi) —S(=O)R$^c$, or
(vii) —SO$_2$R$^c$, and
(b) optionally substituted with from 1 to 3 substituents each of which is independently:
(i) —R$^k$,
(ii) —C$_{1-6}$ alkyl-R$^k$,
(iii) —C(=O)—R$^k$, or
(iv) —C(=O)N(R$^a$)R$^k$, or
(3) —R$^k$;

each R$^a$ and R$^b$ is independently —H or —C$_{1-6}$ alkyl;
each R$^c$ is independently —C$_{1-6}$ alkyl;
each R$^d$ is independently —H, —C$_{1-6}$ alkyl or —C$_{1-6}$ haloalkyl;
each R$^k$ is independently an optionally substituted carbocycle or an optionally substituted heterocycle;
carbocycle in R$^k$ is independently (i) a C$_3$ to C$_8$ monocyclic, saturated or unsaturated ring, (ii) a C$_7$ to C$_{12}$ bicyclic ring system, or (iii) a C$_{11}$ to C$_{16}$ tricyclic ring system, wherein each ring in (ii) or (iii) is independent of, fused to, or bridged with the other ring or rings and each ring is saturated or unsaturated; wherein the carbocycle is optionally substituted with from 1 to 7 substituents each of which is independently
(1) halogen, provided that the ring of the carbocycle substituted with the halogen is aromatic,
(2) —OH,
(3) —C$_{1-6}$ alkyl, optionally mono-substituted with —OH, —O—C$_{1-6}$ alkyl, —CN, —NO$_2$, —C(=O)N(R$^a$R$^b$), —CO$_2$R$^a$, —S(=O)R$^c$, —SO$_2$R$^c$, —SO$_2$N(R$^a$R$^b$), —N(R$^a$)SO$_2$R$^c$, —C$_{3-8}$ cycloalkyl, phenyl, —O-phenyl, or HetB,
(4) —C$_{2-6}$ alkenyl,
(5) —C$_{2-6}$ alkynyl,
(6) —O—C$_{1-6}$ alkyl,
(7) —CN,
(8) —NO$_2$,
(9) —C(=O)N(R$^a$R$^b$),
(10) —CO$_2$R$^a$,
(11) —S(=O)R$^c$,
(12) —SO$_2$R$^c$,
(13) —N(R$^a$)SO$_2$R$^c$,
(14) —SO$_2$N(R$^a$R$^b$),
(15) —C$_{3-8}$ cycloalkyl,
(16) phenyl,
(17) —O-phenyl, or
(18) HetB;

heterocycle in R$^k$ is independently (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to the other ring or rings and each ring is saturated or unsaturated; wherein the monocyclic ring, bicyclic ring system, or tricyclic ring system contains from 1 to 6 heteroatoms independently selected from N, O and S; wherein any one or more of the nitrogen and sulfur heteroatoms is optionally oxidized, and any one or more of the nitrogen heteroatoms is optionally quaternized; and wherein the heterocycle is optionally substituted with from 1 to 7 substituents each of which is independently
(1) halogen, provided that the ring of the heterocycle substituted with the halogen is aromatic,
(2) —OH,
(3) —C$_{1-6}$ alkyl, optionally mono-substituted with —OH, —O—C$_{1-6}$ alkyl, —CN, —NO$_2$, —C(=O)N(R$^a$R$^b$), —CO$_2$R$^a$, —S(=O)R$^c$, —SO$_2$R$^c$, —SO$_2$N(R$^a$R$^b$), —N(R$^a$)SO$_2$R$^c$, —C$_{3-8}$ cycloalkyl, phenyl, —O-phenyl, or HetB,
(4) —C$_{2-6}$ alkenyl,
(5) —C$_{2-6}$ alkynyl,
(6) —O—C$_{1-6}$ alkyl,
(7) —CN,
(8) —NO$_2$,
(9) —C(=O)N(R$^a$R$^b$),
(10) —CO$_2$R$^a$,
(11) —S(=O)R$^c$,
(12) —SO$_2$R$^c$,
(13) —N(R$^a$)SO$_2$R$^c$,
(14) —SO$_2$N(R$^a$R$^b$),
(15) —C$_{3-8}$ cycloalkyl,
(16) phenyl,
(17) —O-phenyl, or
(18) HetB;
and with the proviso that (a) when a ring nitrogen is part of a non-aromatic ring in R$^k$, the nitrogen is a tertiary amine or is quaternized and (b) when a ring sulfur is part of a non-aromatic ring and is attached to ring carbons in R$^k$, the sulfur is a sulfoxide (—S(=O)—) or a sulfone (—S(O$_2$)—);

each HetA is independently a 5- or 6-membered heteroaromatic ring containing from 1 to 3 heteroatoms independently selected from O and S, wherein the heteroaromatic ring is optionally fused with a benzene ring; wherein the optionally fused heteroaromatic ring is optionally substituted with from 1 to 4 substituents each of which is independently halo, —C$_{1-6}$ alkyl, or —O—C$_{1-6}$ alkyl;
each HetB is independently a 5- or 6-membered saturated or unsaturated heterocyclic ring containing from 1 to 4 heteroatoms independently selected from N, O and optionally oxidized S, wherein the heterocyclic ring is optionally fused with a benzene ring; and wherein the optionally fused heterocyclic ring is optionally substituted with from 1 to 7 substituents each of which is independently halogen, provided that the ring to which the halogen is attached is aromatic, —C$_{1-6}$ alkyl, —O—C$_{1-6}$ alkyl, or —CO$_2$R$^a$; and with the proviso that when HetB is not aromatic, then any ring nitrogen is a tertiary amino nitrogen and any ring sulfur that is attached to ring carbons is a sulfoxide or a sulfone; and
s and t are each an integer equal to zero or 1, with the proviso that s+t=1 or 2.

An embodiment of the present invention is the process as just described, wherein X is N, the integer s=1, and the integer t=1. In other words, in this embodiment the process of the invention is limited to the alkylation of piperazines.

Another embodiment of the present invention is the process as originally described above, wherein X is CH, the integer s=1, and the integer t=1. In other words, in this embodiment the process of the invention is limited to the alkylation of piperidines.

Another embodiment of the present invention is the process as originally described above, wherein X is CH, one of the integers s and t=1, and the other of the integers s and t=0. In other words, in this embodiment the process of the invention is limited to the alkylation of pyrrolidines.

Still another embodiment of the present invention is the process as originally described above, wherein X is N, one of the integers s and t=1, and the other of the integers s and t=0. In other words, in this embodiment the process of the invention is limited to the alkylation of imidazolidines.

The process of the present invention can provide reductively alkylated cyclic amines containing π-deficient heteroaryl rings in high yield and in high purity and free of amine-borane complex, wherein any amine-borane complexes formed as a result of the use of the borohydride reducing agent in the reductive alkylation can be efficiently cleaved for removal by alcoholysis in the presence of a Pt oxide or halide or a Pd oxide or halide.

Various other embodiments, aspects and features of the present invention are either further described in or will be apparent from the ensuing description, examples, and appended claims.

DETAILED DESCRIPTION OF THE INVENTION

A compound of Formula (I) is alternatively referred to herein more simply as "Compound I". Similarly, an aldehyde of Formula (II) is alternatively referred to as "aldehyde II", a cyclic amine compound of Formula (III) is alternatively referred to as "cyclic amine III", and an iminium salt of Formula (IV) is alternatively referred to as "iminium salt IV".

The present invention is directed to improved processes for preparing alkylated cyclic amines via reductive alkylation with a borohydride. The present invention includes the process comprising Steps A, B and C as set forth above in the Summary of the Invention.

In this process, the $R^1$ group in the definition of Compound I, aldehyde II and iminium salt IV is a heteroaryl which is (i) a 5- or 6-membered heteroaromatic ring or (ii) a 9- or 10-membered fused, bicyclic ring system in which both rings are aromatic rings and at least one of the rings is a heteroaromatic ring; wherein the heteroaryl contains at least one carbon atom, one or more nitrogen atoms, optionally one or more O atoms, and optionally one or more S atoms; wherein at least one ring nitrogen in the heteroaryl has an unbonded electron pair that is not utilized in the aromatic π system of the heteroaryl; and wherein the heteroaryl is optionally substituted with from 1 to 5 substituents each of which is independently: (1) halo, (2) —$C_{1-6}$ alkyl, (3) —$C_{1-6}$ alkyl mono-substituted with —OH, —O—$C_{1-6}$ alkyl, —$CO_2R^a$, —S(=O)$R^c$, or —$SO_2R^c$, (4) —O—$C_{1-6}$ alkyl, (5) —O—$C_{1-6}$ alkyl mono-substituted with —OH, —O—$C_{1-6}$ alkyl, —$CO_2R^a$, —S(=O)$R^c$, or —$SO_2R^c$, (6) —OH, (7) —$CO_2R^a$, (8) —C(=O)N($R^aR^b$), (9) —S(=O) $R^c$, (10) —$SO_2R^c$, (11) aryl, optionally substituted with from 1 to 5 substituents each of which is independently halo, —OH, —$C_{1-6}$ alkyl, —O—$C_{1-6}$ alkyl, —$CO_2R^a$, —S(=O) $R^c$, or —$SO_2R^c$, (12)—$C_{1-6}$ alkyl-aryl, wherein the aryl is optionally substituted with from 1 to 5 substituents each of which is independently halo, —OH, —$C_{1-6}$ alkyl, —O—$C_{1-6}$ alkyl, —$CO_2R^a$, —S(=O)$R^c$, or —$SO_2R^c$, (13) HetA, or (14)—$C_{1-6}$ alkyl-HetA.

In one embodiment, $R^1$ is a heteroaryl which is (i) a 5- or 6-membered heteroaromatic ring containing a total of from 1 to 4 heteroatoms independently selected from 1 to 4 N atoms, from zero to 2 O atoms, and from zero to 2 S atoms, or (ii) a fused, bicyclic heteroaromatic ring system containing two 6-membered rings both of which are aromatic and at least one of which contains a heteroatom; wherein the heteroaromatic ring system contains a total of from 1 to 6 heteroatoms independently selected from 1 to 6 N atoms, from zero to 3 O atoms, and from zero to 3 S atoms; wherein at least one ring nitrogen in the heteroaryl has an electron pair that is not utilized in the aromatic π system of the heteroaryl; and wherein the heteroaryl is optionally substituted with from 1 to 5 substituents (or from 1 to 4 substituents, or from 1 to 3 substituents, or with 1 or 2 substituents, or with 1 substituent) each of which is independently one of substituents (1) to (14) as set forth in the definition of $R^1$ above. In an aspect of this embodiment, the heteroaryl is optionally substituted with from 1 to 3 substituents (or with 1 or 2 substituents, or with 1 substituent) each of which is independently: (i) fluoro, chloro, or bromo, (ii) —$C_{1-4}$ alkyl, (iii) —O—$C_{1-4}$ alkyl, (iv) phenyl, optionally substituted with from 1 to 4 substituents each of which is independently fluoro, chloro, bromo, —$C_{1-4}$ alkyl, or —O—$C_{1-14}$ alkyl, or (v) —$(CH_2)_{1-2}$-phenyl, wherein the phenyl is optionally substituted with from 1 to 4 substituents each of which is independently fluoro, chloro, bromo, —$C_{1-4}$ alkyl, or —O—$C_{1-4}$ alkyl.

In another embodiment, $R^1$ is a heteroaryl selected from the group consisting of pyridinyl, pyrazolyl, imidazolyl, triazolyl, tetrazolyl, thiazolyl, isothiazolyl, oxazolyl, isooxazolyl, pyridazinyl, pyrimidinyl, pyrazinyl, triazinyl, quinolinyl, isoquinolinyl, quinazolinyl, and naphthyridinyl; wherein the heteroaryl is optionally substituted with from 1 to 5 substituents (or from 1 to 4 substituents, or from 1 to 3 substituents, or with 1 or 2 substituents, or with 1 substituent) each of which is independently one of substituents (1) to (14) as set forth in the definition of $R^1$ above. In an aspect of this embodiment, the heteroaryl is optionally substituted with from 1 to 3 substituents each of which is independently one of substituents (i) to (v) as set forth in the last sentence of the preceding paragraph.

In another embodiment, $R^1$ is a heteroaryl selected from the group consisting of pyridinyl, quinolinyl, isoquinolinyl, imidazolyl, and pyrazolyl; wherein the heteroaryl is optionally substituted with from 1 to 3 substituents (or with 1 or 2 substituents, or with 1 substituent) each of which is independently one of substituents (1) to (14) as set forth in the definition of $R^1$ above. In an aspect of this embodiment, the heteroaryl is optionally substituted with from 1 to 3 substituents each of which is independently one of substituents (i) to (v) as set forth in the last sentence of the next to preceding paragraph.

In still another embodiment, $R^1$ is pyridinyl optionally substituted with from 1 to 3 substituents each of which is independently fluoro, chloro, bromo, —$C_{1-4}$ alkyl (e.g., methyl, ethyl, or isopropyl), or —O—$C_{1-4}$ alkyl (e.g., methoxy, ethoxy or isopropyloxy). In an aspect of this embodiment, $R^1$ is pyridinyl optionally substituted with 1 or 2 substituents each of which is independently fluoro, chloro, bromo, methyl, or methoxy. In another aspect of this embodiment, $R^1$ is 3-pyridinyl.

It is understood that in the aldehyde of Formula II (i.e., $R^1$—CHO) the heteroaryl group defined by $R^1$ is attached to the CHO group via a ring carbon in the heteroaryl.

In the process, the $R^2$, $R^3$, $R^5$ and $R^6$ groups in Compound I, cyclic amine III, and iminium salt IV are defined as follows: Each of $R^2$, $R^3$, $R^5$ and $R^6$ is independently: (1) —H, (2) —$C_{1-6}$ alkyl, (3) —$C_{1-6}$ alkyl mono-substituted with —OH, —O—$C_{1-6}$ alkyl, —$CO_2R^a$, —S(=O)$R^c$, or —$SO_2R^c$, (4) —O—$C_{1-6}$ alkyl, (5) —O—$C_{1-6}$ alkyl mono-substituted with —OH, —O—$C_{1-6}$ alkyl, —$CO_2R^a$, —S(=O)$R^c$, or —$SO_2R^c$, (6) —OH, (7) —$CO_2R^a$, (8) —C(=O)N($R^aR^a$), (9) —S(=O)$R^c$, (10) —$SO_2R^c$, (11) aryl, optionally substituted with from 1 to 5 substituents each of which is independently halo, —OH, —$C_{1-6}$ alkyl, —O—$C_{1-6}$ alkyl, —$CO_2R^a$, —S(=O)$R^c$, or —$SO_2R^c$, (12) —$C_{1-6}$ alkyl-aryl, wherein the aryl is optionally substituted with from 1 to 5 substituents each of which is independently halo, —OH, —$C_{1-6}$ alkyl, —O—$C_{1-6}$ alkyl, —$CO_2R^a$, —S(=O)$R^c$, or —$SO_2R^c$, (13) HetA, or (14) —$C_{1-6}$ alkyl-HetA.

In one embodiment, any two of $R^2$, $R^3$, $R^5$ and $R^6$ are H; and the other two of $R^2$, $R^3$, $R^5$ and $R^6$ are each independently as defined above. In an aspect of this embodiment, any two of $R^2$, $R^3$, $R^5$ and $R^6$ are H; and the other two of $R^2$, $R^3$, $R^5$ and $R^6$ are each independently: (i) —H, (ii) —$C_{1-14}$ alkyl, (iv) —O—$C_{1-4}$ alkyl, (v) —$CO_2R^a$, (vi) —C(=O)N ($R^aR^d$), (vii) phenyl, optionally substituted with from 1 to 4 substituents each of which is independently fluoro, chloro, bromo, —$C_{1-4}$ alkyl, or —O—$C_{1-4}$ alkyl, or (viii) —$(CH_2)_{1-2}$-phenyl, wherein the phenyl is optionally substituted with from 1 to 4 substituents each of which is independently fluoro, chloro, bromo, —$C_{1-4}$ alkyl, or —O—$C_{1-4}$ alkyl.

In another embodiment, $R^2$ and $R^6$ are each H; and each of $R^3$ and $R^5$ is independently one of groups (1) to (14) as defined above. In an aspect of this embodiment, $R^2$ and $R^6$ are each H; and each of $R^3$ and $R^5$ is independently one of groups (i) to (viii) as defined above.

In another embodiment, $R^2$ and $R^6$ are both H; one of $R^3$ and $R^5$ is H, and the other of $R^3$ and $R^5$ is —C(=O)NH(—$C_{1-6}$ alkyl) or —C(=O)NH(—$C_{1-6}$ fluoroalkyl). In an aspect of this embodiment, $R^2$ and $R^6$ are both H; one of $R^3$ and $R^5$ is H, and the other of $R^3$ and $R^5$ is —C(=O)NHC(CH3)$_3$ or —C(=O)NHCH$_2$CF$_3$. In another aspect of this embodiment, each of $R^2$, $R^3$, and $R^6$ is H; and $R^5$ is —C(=O)NHC(CH3)$_3$.

In still another embodiment, each of $R^2$, $R^3$, $R^5$ and $R^6$ is H.

In the process of the invention, $R^4$ in Compound I, cyclic amine III, and iminium salt IV is:

(1) —H,
(2) —$C_{1-20}$ alkyl, which is:
  (a) optionally substituted with from 1 to 7 substituents each of which is independently: (i) —OH, (ii) —$C_{1-6}$ alkyl, (iii) —O—$C_{1-6}$ alkyl, (iv) —CO$_2$R$^a$, (v) —C(=O)N(R$^a$R$^b$), (vi) —S(=O)R$^c$, or (vii) —SO$_2$R$^c$, and
  (b) optionally substituted with from 1 to 3 substituents each of which is independently: (i) —R$^k$, (ii) —$C_{1-6}$ alkyl-R$^k$, (iii) —C(=O)—R$^k$, or (iv) —C(=O)N(R$^a$)R$^k$, or
(3) —R$^k$.

In one embodiment, $R^4$ is —$C_{1-10}$ alkyl, which is:
(i) substituted with 1 or 2 substituents each of which is independently —OH, —O—$C_{1-14}$ alkyl, or —$C_{1-4}$ alkyl;
(ii) substituted with —$C_{1-4}$ alkyl-R$^u$, wherein R$^u$ is —$C_{3-6}$ cycloalkyl, aryl selected from phenyl and naphthyl, or HetC, wherein HetC is a 5- or 6-membered heteroaromatic ring containing from 1 to 3 heteroatoms independently selected from N, O and S; and wherein aryl or HetC is optionally substituted with from 1 to 4 substituents each of which is independently halogen, —OH, —$C_{1-6}$ alkyl, or —O—$C_{1-6}$ alkyl; and
(iii) substituted with —C(=O)N(R$^a$)R$^v$, wherein R$^a$ is H, methyl, or ethyl; and R$^v$ is cyclopentyl, indanyl, tetralin, chroman, thiochroman, or dioxoisothiochroman, any one of which is optionally substituted with from 1 to 4 substitutents each of which is independently halogen, provided that the ring to which the halogen is attached is aromatic, —OH, —$C_{1-6}$ alkyl, —O—$C_{1-6}$ alkyl, or phenyl.

In an aspect of the preceding embodiment, $R^4$ is:

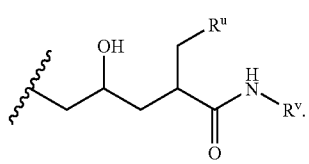

(V)

In another aspect of the preceding embodiment, $R^4$ is:

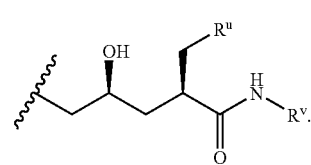

(VI)

In a feature of each of the two preceding aspects, R$^u$ is cyclopropyl, phenyl, pyridinyl, thienyl, or thiazolyl; wherein the phenyl, pyridinyl, thienyl, or thiazolyl is optionally substituted with from 1 to 3 substituents each of which is independently halogen, —$C_{1-6}$ alkyl, or —O—$C_{1-6}$ alkyl.

In another feature of each of the two preceding aspects, R$^u$ is phenyl.

In still another feature of each of the two preceding aspects, R$^v$ is:

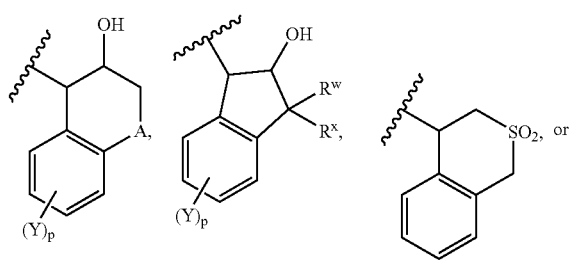

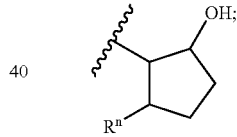

wherein
A is CR$^w$R$^x$ or O;
each Y is independently H, halogen, —$C_{1-6}$ alkyl, or —O—$C_{1-6}$ alkyl;
R$^w$ and R$^x$ are each independently H or —$C_{1-4}$ alkyl;
R" is H, —$C_{1-4}$ alkyl, or phenyl; and
p is an integer from 0 to 2.

In yet another feature of each of the two preceding aspects, R$^v$ is:

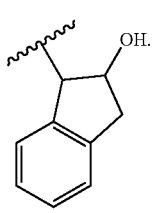

In another aspect of the preceding embodiment, R$^4$ is:

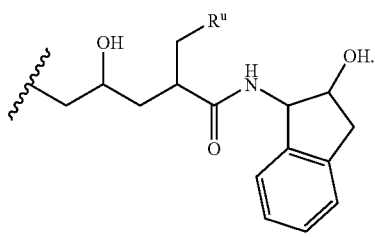

(VII)

In yet another aspect of the preceding embodiment, R$^4$ is:

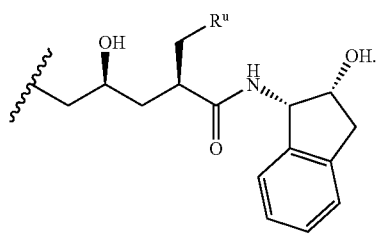

(VIII)

In a feature of this aspect, R$^4$ is:

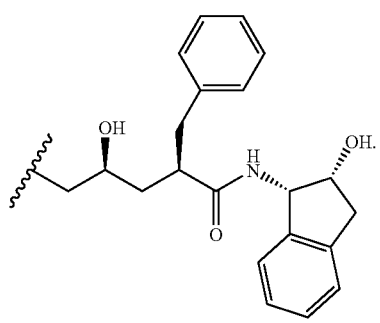

(IX)

Certain of the substituent definitions set forth herein include groups R$^a$ and/or R$^b$. Each R$^a$ and R$^b$ is independently —H or —C$_{1-6}$ alkyl. In one embodiment, each R$^a$ and R$^b$ is independently —H or —C$_{1-4}$ alkyl. In another embodiment, each R$^a$ and R$^b$ is independently —H, methyl, or ethyl. In still another embodiment, each R$^a$ and R$^b$ is independently —H or methyl.

Certain of the substituent definitions set forth herein include the group R$^c$. Each R$^c$ is independently a —C$_{1-6}$ alkyl. In one embodiment, each R$^c$ is independently a —C$_{1-4}$ alkyl. In another embodiment, each R$^c$ is independently methyl or ethyl. In still another embodiment, each R$^c$ is methyl.

The definitions of groups R$^2$, R$^3$, R$^5$, and R$^6$ include the group R$^d$ in —C(=O)N(R$^a$R$^d$), wherein each R$^d$ is independently —H, —C$_{1-6}$ alkyl or —C$_{1-6}$ haloalkyl. In one embodiment, each R$^d$ is independently a —H, —C$_{1-4}$ alkyl or —C$_{1-4}$ haloalkyl. In another embodiment, each R$^d$ is independently a —H, —C$_{1-4}$ alkyl or —C$_{1-4}$ fluoroalkyl. In still another embodiment, each R$^d$ is —C$_{1-4}$ alkyl or —C$_{1-4}$ fluoroalkyl. In an aspect of this embodiment, each R$^d$ is tert-butyl(—C(CH$_3$)$_3$) or 2,2,2-trifluoroethyl(—CH$_2$CF$_3$). In another aspect of this embodiment, each R$^d$ is tert-butyl.

The definition of substituent R$^4$ includes R$^k$ groups, wherein each R$^k$ is independently an optionally substituted carbocycle or an optionally substituted heterocycle, wherein carbocycle and heterocycle are defined above. In one embodiment, each R$^k$ in R$^4$ is independently:

(1) —C$_{3-8}$ cycloalkyl, (2) —C$_{3-8}$ cycloalkyl fused with a —C$_{5-7}$ cycloalkyl ring or with a benzene ring, (3) aryl selected from phenyl, naphthyl, anthracenyl, and phenanthryl, (4) a 5- or 6-membered heteroaromatic ring containing from 1 to 4 heteroatoms independently selected from oxygen, nitrogen and sulfur, (5) a 5- or 6-membered saturated or mono-unsaturated heterocyclic ring containing from 1 to 3 heteroatoms independently selected from oxygen, nitrogen, and optionally oxidized sulfur, or (6) an 8- to 10-membered heterobicyclic ring system in which the rings are fused and each ring is saturated or unsaturated, wherein the ring system contains from 1 to 4 heteroatoms independently selected from oxygen, nitrogen and optionally oxidized sulfur;

wherein the cycloalkyl of (1), the fused cycloalkyl of (2), the aryl of (3), the heteroaromatic ring of (4), the heterocyclic ring of (5), or the heterobicyclic ring system of (6) is optionally substituted with from 1 to 5 substituents each of which is independently:

(1) halogen, provided that the ring to which the halogen is attached is aromatic, (2) —OH, (3) —C$_{1-6}$ alkyl, optionally mono-substituted with —OH, —O—C$_{1-6}$ alkyl, —C$_{3-8}$ cycloalkyl, phenyl, or —O-phenyl, (4) —O—C$_{1-6}$ alkyl, (5) —C$_{3-8}$ cycloalkyl, (6) phenyl, or (7) —O-phenyl;

and with the proviso that:

(a) when a ring nitrogen is part of the heterocyclic ring of (5) or is part of a non-aromatic ring in the heterobicyclic ring system of (6), the nitrogen is a tertiary amine, and (b) when a ring sulfur is part of the heterocyclic ring of (5) or is part of a non-aromatic ring in the heterobicyclic ring system of (6) and is attached to ring carbons therein, the sulfur is a sulfoxide or a sulfone In another embodiment, each R$^k$ in R$^4$ is independently:

(1) —C$_{3-6}$ cycloalkyl (e.g., cyclopropyl or cyclopentyl) optionally mono-substituted with OH, optionally mono- or di-substituted with a —C$_{1-4}$ alkyl, and optionally mono-substituted with phenyl, (2) —C$_{3-6}$ cycloalkyl fused with a benzene ring (e.g., indanyl or tetralin), in which the cycloalkyl is optionally mono-substituted with OH and optionally mono- or disubstituted with a —C$_{1-4}$ alkyl, and in which the benzene ring is optionally substituted with from 1 to 3 substituents, each of which is independently halogen, —C$_{1-4}$ alkyl, or —O—C$_{1-4}$ alkyl, (3) phenyl or naphthyl, either of which is optionally substituted with from 1 to 3 substituents, each of which is independently halogen, —C$_{1-4}$ alkyl, or —O—C$_{1-4}$ alkyl, (4) a 5- or 6-membered heteroaromatic ring selected from the group consisting of pyridinyl, pyrimidinyl, pyradizinyl, pyrazinyl, pyrrolyl, pyrazolyl, imidazolyl, triazolyl, thiazolyl, thienyl, furanyl, and oxazolyl, wherein the heteroaromatic ring is optionally substituted with 1 or 2 substituents each of which is independently halo or —$C_{1-4}$ alkyl, (5) an 8- to 10-membered heterobicyclic ring system selected from the group consisting of chromanyl and dioxoisothiochromanyl, in which the benzene moiety in the ring system is optionally substituted with from 1 to 3 substituents each of which is independently halo or —$C_{1-4}$ alkyl, and in which the heteroatom-containing ring is optionally monosubstituted with OH.

In still another embodiment, each $R^k$ in $R^4$ independently has a definition corresponding to that of $R^u$ or $R^v$ as heretofore defined.

The substituent definitions for $R^1$, $R^2$, $R^3$, $R^5$ and $R^6$ as set forth herein include HetA groups, wherein each HetA is independently a 5- or 6-membered heteroaromatic ring containing from 1 to 3 heteroatoms independently selected from O and S, wherein the heteroaromatic ring is optionally fused with a benzene ring; wherein the optionally fused heteroaromatic ring is optionally substituted with from 1 to 4 substituents each of which is independently halo, —$C_{1-6}$ alkyl, or —O—$C_{1-6}$ alkyl. It is understood that in the case where HetA is a heteroaromatic ring fused with a benzene ring, the optional substituents can be on either or both the benzene ring and the heteroaromatic ring.

In one embodiment, each HetA is a heteroaromatic ring optionally fused with a benzene ring independently selected from the group consisting of pyridinyl, pyrimidinyl, pyradizinyl, pyrazinyl, pyrrolyl, pyrazolyl, imidazolyl, triazolyl, thiazolyl, thienyl, furanyl, oxazolyl, benzimidazolyl, benzothienyl, benzofuranyl, benzoxazolyl, quinolinyl, isoquinolinyl, cinnolinyl, and quinazolinyl; wherein the heteroaromatic ring is optionally substituted with from 1 to 4 substituents each of which is independently halo (e.g., fluoro, chloro, or bromo), —$C_{1-6}$ alkyl (e.g., methyl, ethyl, propyl, or isopropyl), or —O—$C_{1-6}$ alkyl (e.g., methoxy, ethoxy, propoxy, or isopropoxy).

The definition of $R^k$ in $R^4$ as set forth herein includes HetB groups, wherein each HetB is independently a 5- or 6-membered saturated or unsaturated heterocyclic ring containing from 1 to 4 heteroatoms independently selected from N, O and S, wherein the heterocyclic ring is optionally fused with a benzene ring; and wherein the optionally fused heterocyclic ring is optionally substituted with from 1 to 7 substituents each of which is independently halogen, provided that the ring to which the halogen is attached is aromatic, —$C_{1-6}$ alkyl, —O—$C_{1-6}$ alkyl, or —$CO_2R^a$; and with the proviso that when HetB is not aromatic, then any ring nitrogen is a tertiary amino nitrogen and any ring sulfur that is attached to ring carbons is a sulfoxide or a sulfone.

In one embodiment, each HetB is a heteroaromatic ring independently selected from the group consisting of pyridinyl, pyrimidinyl, pyradizinyl, pyrazinyl, pyrrolyl, pyrazolyl, imidazolyl, triazolyl, thiazolyl, thienyl, furanyl, and oxazolyl, wherein the heteroaromatic ring is optionally substituted with 1 or 2 substituents each of which is independently halo or —$C_{1-4}$ alkyl.

It is understood that any embodiment, aspect, or feature of any one of X, $R^1$, $R^2$, $R^3$, $R^4$, $R^5$, $R^6$, $R^a$, $R^b$, $R^c$, $R^d$, $R^k$, HetA, HetB, and the integers s and t can be combined with any embodiment, aspect of feature of any one or more of the others of X, $R^1$, $R^2$, $R^3$, $R^4$, $R^5$, $R^6$, $R^a$, $R^b$, $R^c$, $R^d$, $R^k$, HetA, HetB, and the integers s and t. Each such possible combination, when incorporated into the process of the invention as defined above, represents an embodiment of the process of the present invention.

As used herein, the term "$C_{1-6}$ alkyl" (or "$C_1-C_6$ alkyl") means a linear or branched chain alkyl group having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "—$C_{1-6}$ alkyl-" refers to a $C_1$ to $C_6$ linear or branched alkyl group as just defined which is bivalent. It can alternatively be referred to as "$C_{1-6}$ alkylene" or "$C_{1-6}$ alkanediyl". A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—.

The term "$C_{3-8}$ cycloalkyl" (or "$C_3-C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). Similar terms such as "$C_{3-6}$ cycloalkyl" have an analogous meaning.

The term "halogen" (or "halo") refers to fluorine, chlorine, bromine and iodine (alternatively referred to as fluoro, chloro, bromo, and iodo).

The term "$C_{1-6}$ haloalkyl" (which may alternatively be referred to as "$C_1-C_6$ haloalkyl" or "halogenated $C_1-C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. A class of fluoroalkyls of particular interest with respect to the invention is the series $(CH_2)_{0-4}CF_3$ (i.e., trifluoromethyl, 2,2,2-trifluoroethyl, 3,3,3-trifluoro-n-propyl, etc.).

The term "thienyl" (also known in the art as "thiophenyl") refers to

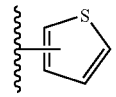

The term "tertiary amine" has its conventional meaning; i.e., it refers to compounds derived from ammonia by replacing all three hydrogens with one or more organic substituents. The tertiary amino nitrogen is typically singly bonded to three carbon atoms. When a ring nitrogen in a non-aromatic ring (e.g., in $R^k$) is a tertiary amine, it is understood that the tertiary amine can be formed either by the ring system itself or by attachment of a suitable substituent on the ring nitrogen, respectively exemplified by structures A and B as follows:

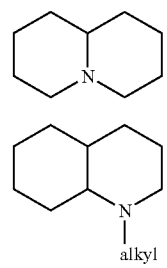

A

B

The term "ring sulfur atom attached to ring carbons" refers to a sulfur atom that is part of a ring by being directly attached (bonded) only to carbon atoms in the ring; i.e., the sulfur atom is not directly attached to any other heteroatom that may be part of the ring. Thus, when the definition of a heterocyclic ring (e.g., in $R^k$) provides that when a ring sulfur is part of a non-aromatic ring and is attached to ring carbons, then any ring sulfur that is attached to ring carbons is a sulfoxide or a sulfone, it is understood that rings such as C and D are permitted (i.e., included in the definition of the ring), but rings such as E and F are not:

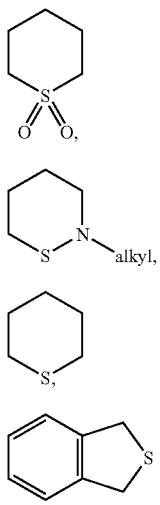

The term "aryl" as used herein refers to an aromatic carbocyclic ring or an aromatic carbocyclic fused ring system. The fused ring system contains two or more carbocyclic rings in which each ring shares two adjacent carbon atoms with at least one other ring. The aryl group may be attached to the rest of the molecule at any carbon atom which results in a stable compound. A subset of aryl groups particularly suitable for use in the present invention (e.g., in the definition of $R^k$) includes those selected from phenyl, naphthyl, anthryl (also referred to as "anthracenyl"), and phenanthryl. Another particularly suitable subset of aryl groups is phenyl and naphthyl. Still another particularly suitable subset of aryl groups is phenyl per se.

Unless expressly stated to the contrary, any heterocyclic ring defined or described herein (e.g., HetA, HetB, HetC, and $R^k$ in part) may be attached to the rest of the molecule of which it is a part via any heteroatom or carbon atom in the ring, provided that attachment results in the creation of a stable structure. When the heterocyclic ring has substituents, unless expressly stated otherwise, it is understood that the substituents may be attached to any atom in the ring, whether a heteroatom or a carbon atom, provided that a stable chemical structure results.

Unless expressly stated to the contrary, an "unsaturated" ring is a partially or fully unsaturated ring.

Unless expressly stated to the contrary, all ranges cited herein are inclusive. For example, a heterocyclic ring described as containing from "1 to 4 heteroatoms" means the ring can contain 1, 2, 3 or 4 heteroatoms.

When any variable (e.g., $R^a$, $R^b$, $R^c$, or $R^k$) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "each aryl is optionally substituted with from 1 to 5 substituents . . . ") includes mono- and poly-substitution by a named substituent to the extent such single and multiple substitution (including multiple substitution at the same site) is chemically allowed.

The symbol "⌇" in front of an open bond in the structural formula of a group marks the point of attachment of the group to the rest of the molecule.

The terms "carbaldehyde" and "carboxaldehyde" are used interchangeably herein.

Aldehyde II and cyclic amine III as defined herein can have asymmetric centers and can be employed in the process of the invention as mixtures of stereoisomers or as individual diastereomers, or enantiomers. Accordingly, the resulting product of the process of the invention (i.e., Compound I) can be obtained as a mixture of stereoisomers or as individual diastereomers or enantiomers.

Step A of the process of the invention comprises reacting aldehyde II with cyclic amine III in an organic solvent and in the presence of a $C_{1-6}$ alkylcarboxylic acid and with removal of by-product water to form a reaction mixture comprising iminium salt IV. The cyclic amines of Formula III include imidazolines (i.e., X=N and s=1 and t=0, or X=N and s=0 and t=1), pyrrolidines (X=CH and s=1 and t=1, or X=CH and s=0 and t=1), piperazines (X=N and s=t=1), and piperidines (X=CH and s=t=1). In one embodiment, cyclic amine III is a piperazine or a piperidine. In another embodiment, cyclic amine III is a piperazine.

The aldehyde and cyclic amine reactants suitable for use in the process of the invention can be prepared by methods known in the art. Pyridine carbaldehydes, for example, can be prepared by methods (or routine variations thereof) disclosed in R. H. Mizzoni, "Pyridine Aldehydes and Ketones", Chapter XIV in *Pyridine and its Derivatives*, edited by E. Klingsberg, Wiley Interscience, New York, 1964 and in the supplement thereto of the same name, edited by R. A. Abramovitch, 1975. Methods for preparing pyridine carbaldehydes are also disclosed in *Rodd's Chemistry of Carbon Compounds*, Vol. IV-F, Elsevier, 1976, pages 181–183. As another example, piperazines can be prepared in accordance with the methods disclosed in *Rodd's Chemistry of Carbon Compounds*, Vol. IV-IJ, Elsevier, 1989, pages 287–294, or routine variations thereof. More particularly, piperazines having an $R^4$ substituent of Formula (V), (VI), (VII), (VIII), or (IX) can be prepared in accordance with the methods described in U.S. Pat. No. 5,413,999 (see, e.g., Scheme II), U.S. Pat. No. 5,646,148 (see, e.g., Scheme II), and WO 01/38332 (see, e.g., Scheme 1), or by routine variations thereof.

Quinolines may be prepared by the Friedlander synthesis wherein an ortho-acylarylamine condenses with a ketone or aldehyde by base or acid catalysis to yield the quinoline as disclosed in Cheng et al., *Org. React.* 1982, 28: 37. Isoquinolines may be prepared the Pomeranz-Fritsch synthesis wherein an aryl aldehyde is condensed with aminoacetal to form an aldimine which is subsequently cyclized by treatment with acid as reviewed in Gensler, *Org. React.* 1951, 6: 191. Quinolines, isoquinolines and pyridines may be halogenated and subsequently lithiated with LDA or n-BuLi by exchange and finally formylated by treatment with ethyl formate or DMF as disclosed in Joule and Mills, *Heterocyclic Chemistry*, IV ed., Blackwell Science Ltd., United Kingdom, 2000; p 77–83. 1,3-azoles may be lithiated directly in the 2-position by treatment with n-BuLi and subsequently formylated by addition of ethyl formate, ibid, p. 399.

The carboxylic acid employed in Step A is a $C_{1-6}$ alkylcarboxylic acid, and in one embodiment is a $C_{1-4}$ alkylcarboxylic acid. The acid is believed to act as a catalyst for the alkylation by protonating the aldehyde to make it more electrophilic. Suitable acids include acetic acid, propionic acid, n-butyric acid, isobutyric acid, n-valeric acid, and isovaleric acid. In a preferred embodiment of the process of the invention, the carboxylic acid is acetic acid.

The solvent employed in the imine salt formation of Step A can be any organic compound which under the reaction conditions employed is in the liquid phase, is chemically inert, and will dissolve, suspend, and/or disperse aldehyde II, piperazine III, and the $C_{1-6}$ alkylcarboxylic acid so as to permit the reaction to proceed. The solvent can be an alcohol. Suitable alcohols include $C_1$–$C_6$ alkyl alcohols, such as methanol, ethanol, n-propanol and isopropanol. The solvent is preferably an aprotic solvent. Suitable aprotic solvents include hydrocarbons (i.e., aliphatic, alicyclic and aromatic hydrocarbons), halogenated hydrocarbons, ethers (i.e., mono-, di- and poly-ethers). Exemplary aprotic solvents include pentane, hexane, carbon tetrachloride, chloroform, methylene chloride, 1,2-dichloroethane, 1,1,2-trichloroethane, 1,1,2,2-tetrachloroethane, cyclohexane, toluene, o- and m- and p-xylene, ethylbenzene, chlorobenzene, ethyl ether, MTBE, THF, dioxane, DME, anisole, phenetole. Tertiary amides such as DMAC, and DMF can also be employed as aprotic solvents in Step A.

In one embodiment, the solvent employed in Step A is selected from the group consisting of $C_5$–$C_{10}$ linear and branched alkanes, $C_5$–$C_{10}$ cycloalkanes, $C_6$–$C_{14}$ aromatic hydrocarbons, di-$C_1$–$C_6$ alkyl ethers, $C_1$–$C_6$ linear and branched alkanes substituted with two —O—$C_1$–$C_6$ alkyl groups (which are the same or different), $C_4$–$C_8$ cyclic ethers and diethers, and $C_6$–$C_{10}$ aromatic ethers. In another embodiment, the solvent employed in Step A is an ether. In an aspect of the preceding embodiment, the ether is THF, MTBE, or DME.

Step A is suitably conducted at a temperature in the range of from about 0 to about 30° C., and is typically conducted at a temperature in the range of from about 10 to 30° C. (e.g., from about 15 to about 28° C.), and is more typically conducted at a temperature in the range of from about 15 to about 25° C. (e.g., from about 18 to about 25° C.).

Optimal conversion of cyclic amine III and optimal formation of iminium salt IV is normally desired in Step A, and relative proportions of reactants and reagents suitable for this purpose are typically employed. Aldehyde II is suitably employed in an amount in the range of from about 1 to about 5 moles per mole of cyclic amine III. In one embodiment, aldehyde II is employed in an amount in the range of from about 1 to about 2 moles per mole of cyclic amine III. In another embodiment, the aldehyde is employed in an amount in the range of from about 1.0 to about 1.5 moles (e.g., from about 1.0 to about 1.3 moles) per mole of cyclic amine III.

The $C_{1-6}$ alkylcarboxylic acid is suitably employed in Step A in an amount in the range of from about 1 to about 3 equivalents per equivalent of amino groups present in cyclic amine III. In one embodiment, the alkylcarboxylic acid is employed in an amount in the range of from about 1 to about 2.5 equivalents (e.g., from about 1.1 to about 2.0 equivalents) per equivalent of amino groups present in cyclic amine III. In another embodiment, the alkylcarboxylic acid is employed in an amount in the range of from about 1.5 to about 2.0 equivalents (e.g., from about 1.6 to about 2.0 equivalents) per equivalent of amino groups present in cyclic amine III. When the number of equivalents of alkylcarboxylic acid exceeds the number of equivalents of amino groups in cyclic amine III in Step A, amine carboxylate salts can form in addition to the iminium salt. Accordingly, although Formula (IV) depicts only the iminium salt, it is understood that some or all of any other amino groups present in iminium salt IV can be present in the form of a carboxylate salt as well. For example, when cyclic amine III is a piperazine (i.e., X=N, s=1, and t=1; see, e.g., piperazine 3 below), one piperazinyl nitrogen forms part of the iminium salt, and the other piperazinyl nitrogen can form an ammonium carboxylate salt.

The reaction of Step A is an equilibrium reaction. Removal of by-product water drives the reaction toward formation of the iminium salt and thereby can increase the yield of the salt. The by-product water can be removed in Step A either during or after or both during and after the reaction of aldehyde II with cyclic amine III. Accordingly, it is understood that the phrase "with removal of by-product water" refers to removal of water during the reaction of Step A, after the Step A reaction is complete, or partly during the Step A reaction and partly after completion of the Step A reaction. The water can be removed during or after the reaction of Step A by use of a dehydrating agent or by distillation. The water is preferably removed by conducting the reaction of Step A in the presence of a dehydrating agent. Suitable dehydrating agents include molecular sieves, silica gel, and anhydrous salts that are chemically inert under the conditions employed in Step A (e.g., magnesium sulfate or sodium sulfate). The dehydrating agent is preferably molecular sieves.

The reaction time for Step A can vary widely depending upon (i) the choice and relative proportions of aldehyde II, cyclic amine III, and alkylcarboxylic acid, (ii) the choice of solvent and temperature, and (iii) the level of conversion desired. The reaction is nonetheless usually complete in about 24 hours or less (e.g., about 12 hours or less), and is typically complete in about 8 hours or less, and is often complete in about 4 hours or less (e.g., in from about 0.1 to about 2 hours).

The order of addition of the reactants and reagents to the reaction vessel (or reaction "pot") in Step A is not critical. The reactants and reagents can, for example, be added concurrently, either together or separately, or they can be added sequentially in any order. In one embodiment, the cyclic amine m is first added to the solvent to form a solution, suspension or dispersion of the amine in the solvent, followed by addition of aldehyde II, the carboxylic acid, and a dehydrating agent (e.g., molecular sieves). The reaction mixture is then brought to reaction temperature and the mixture aged until the desired degree of conversion is achieved. The desired degree of conversion is typically complete conversion of cyclic amine III. As used here and elsewhere in the application, the term "aging" and variants thereof (e.g., "aged") mean allowing the reactants (aldehyde II and cyclic amine III in Step A) to stay in contact for a time and under conditions effective for achieving the desired degree of conversion. The aging is typically conducted until the reaction is complete. The Step A reaction mixture is optionally agitated (e.g., stirred) during addition of the reactants and reagents to the solvent and optionally also during any subsequent aging. When the iminium salt IV formed in Step A is soluble in the solvent, it can be recovered by conventional means such as by filtration to remove the dehydrating agent, concentrating the filtrate by evaporative removal of a portion of the solvent, and then cooling the concentrated solution to precipitate the salt. However, in the process of the invention the Step A reaction mixture comprising the iminium salt is employed directly in Step B.

In Step B of the process of the invention, a tetrahydroborate salt is added to the Step A reaction mixture to obtain a product comprising Compound I and one or more borane complexes thereof. The tetrahydroborate salt is suitably an alkali metal salt or a quaternary ammonium salt of tetrahydroborate. A class of tetrahydroborate salts suitable for use in Step B is a salt selected from the group consisting of NaBH$_4$, LiBH$_4$, KBH$_4$, and ((R*)$_4$N)BH$_4$ wherein R* is H or C$_{1-6}$ alkyl. A sub-class of tetrahydroborate salts suitable for use in Step B is a salt selected from the group consisting of NaBH$_4$, LiBH$_4$, KBH$_4$, NH$_4$BH$_4$, N(Me)$_4$BH$_4$, N(Et)$_4$BH$_4$, N(iso-Pr)$_4$BH$_4$, and N(iso-Bu)$_4$BH$_4$. In a preferred embodiment of the process of the invention, the tetrahydroborate salt is NaBH$_4$.

Optimal conversion of iminium salt IV and optimal formation of Compound I, whether as free base or in the form of a borane complex, is normally desired in Step B, and an amount of tetrahydroborate salt suitable for this purpose is employed. The tetrahydroborate salt is suitably added to the Step A reaction mixture in an amount in the range of from about 0.8 to about 5 moles per mole of cyclic amine III employed in Step A. In one embodiment, tetrahydroborate is employed in an amount in the range of from about 0.8 to about 4 moles (e.g., from about 0.8 to about 1.3 moles) per mole of cyclic amine III. In another embodiment, the tetrahydroborate salt is employed in an amount in the range of from about 1.0 to about 1.5 moles (e.g., from about 1.0 to about 1.2 moles) per mole of cyclic amine III.

Step B is suitably conducted at a temperature in the range of from about 0 to about 30° C., and is typically conducted at a temperature in the range of from about 10 to 30° C. (e.g., from about 15 to about 28° C.), and is more typically conducted at a temperature in the range of from about 15 to about 25° C. (e.g., from about 18 to about 25° C.).

The reaction time for Step B can vary widely depending upon (i) the choice and relative amount of tetrahydroborate salt employed, (ii) the choice of temperature, and (iii) the level of conversion desired. The reaction is nonetheless usually complete in about 24 hours or less, and is typically complete in about 12 hours or less, and is often complete in about 6 hours or less (e.g., in from about 0.5 to about 5 hours).

The tetrahydroborate salt is suitably charged to the reaction vessel containing the Step A reaction mixture continuously or intermittently over a period of time while maintaining the temperature of the mixture at or below reaction temperature, after which the reaction mixture is aged at reaction temperature for a time sufficient to achieve the desired degree of conversion (which is typically complete conversion) of iminium salt IV. The reaction mixture can optionally be agitated (e.g., stirred) during addition of the tetrahydroborate salt and during the subsequent aging.

While not wishing to be bound by any particular theory, it is believed that several reducing species can be acting in Step B to reduce iminium salt IV. The tetrahydroboride itself can reduce the iminium salt directly. At the same time, the tetrahydroboride can react with any other amine carboxylate salts that may be present in salt IV forming a carboxylate salt of the tetrahydroborate counterion (e.g., sodium acetate from NaBH$_4$), hydrogen and amine borane complexes. In particular, relatively stable borane complexes can be formed with the reactive π-deficient heteroaryl group R$^1$ in salt IV (i.e., complex formation occurs at the ring nitrogen in R$^1$ having an unbonded electron pair that is not utilized in the aromatic π system). These amine boranes can also participate in the reduction of the iminium salt. Furthermore, the Step A reaction mixture to which the tetrahydroborate salt is added in Step B can contain alkylcarboxylic acid, since the carboxylic acid is typically employed in Step A in an amount in excess of that consumed via amine salt formation. Acylation of the tetrahydroboride with the excess carboxylic acid can occur in Step B in a stepwise manner, as exemplified here for NaBH$_4$ and acetic acid:

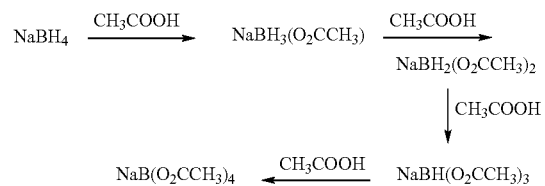

Each successive acylation is slower than the previous one and the reducing strength of each successive acylated hydride is lower than that of its precursor. Nonetheless, these acylated borohydrides, even the trialkylcarboxyborohydrides, can participate in the reduction of the iminium salts.

The product of Step B comprises Compound I in free form and in the form of one or more borane complexes. In particular, at least some of Compound I in the Step B product is in the form of a highly stable borane complex with the ring nitrogen in the R$^1$ heteroaryl group having an unbonded electron pair that is not utilized in the aromatic π system of the heteroaryl. The amount of borane complex present in the Step B product can be determined via HPLC using UV detection.

The Step B product is typically recovered and/or cleaned up prior to employment in Step C of the process of the invention. For example, when a dehydrating agent (e.g., molecular sieves) is employed in Step A, the agent is removed by filtration and washed with the same solvent that was originally employed in Step A, the filtrates combined and quenched with an aqueous salt solution (e.g., brine) at neutral or midly acidic pH. A midly acidic quench has the advantage of removing some of the amine-borane complexes that may be present, but does not remove the relatively stable borane complexes formed with the π-deficient heteroaryl. After the quench, the pH can be adjusted to give a basic solution, the aqueous and organic solvent layers separated, the aqueous layer discarded, and the organic layer employed in Step C. Alternatively, the product of Compound I and its borane complexes can be recovered from the organic layer (e.g., by concentrating the solution via thermal and/or vacuum removal of solvent and then cooling the concentrated solution to precipitate the product) and re-dissolved in another solvent for use in Step C.

In Step C, the product of Step B is treated with a catalyst selected from the group consisting of Pt oxide, Pt halide, Pd oxide and Pd halide in the presence of an alcohol to cleave the one or more borane complexes and thereby obtain the compound of Formula (I) substantially free of any borane complex thereof. The term "substantially free of borane complex" means that less than 10 weight percent, preferably less than 5 weight percent, and more preferably less than 1 weight % (e.g., less than 0.5 wt. %) of the compound of Formula (I) is present (e.g., in a reaction mixture, in solution, or as an isolated material) in the form of a borane complex. In the most preferred case, Compound I substantially free of borane complex refers to Compound I with no detectable amount of borane complex as determined by conventional analytical means (e.g., as determined by HPLC).

In one embodiment of Step C, the catalyst is Pt oxide or Pt halide (e.g., Pt chloride or Pt bromide). In a preferred embodiment, the catalyst is Pt oxide (PtO$_2$). Pt catalysts are preferred; they are typically more efficient and easy to recycle. The catalyst in Step C can be employed in a "catalytic amount"; i.e., in any amount that allows the reaction (or treatment) to proceed under less extreme conditions (e.g., at a lower reaction temperature) and/or in a shorter reaction time compared to the reaction conditions and/or reaction time in the absence of the catalyst. The amount of catalyst employed in Step C is generally a substoichiometric amount of the catalyst relative to the reactants, and herein is suitably from about 0.001 to less than 1 mole (e.g., from about 0.005 to about 0.5 mole) per mole of reactant and is typically from about 0.01 to about 0.2 mole (e.g., from about 0.05 to about 0.15 mole) per mole of reactant. In one embodiment, the amount of catalyst is from about 0.08 to about 0.10 mole per mole of reactant. The reactant in Step C is the borane-complexed portion of Compound I in the product of Step B. The amount of Compound I-borane complex can be determined by HPLC. Alternatively, the amount of catalyst employed can be based upon the molar amount of cyclic amine III initially employed in Step A. This approach avoids the need to determine the amount of borane complex, but has the disadvantage of overestimating the amount of catalyst required in that it assumes that complete conversion of cyclic amine III was desired and achieved and that all of the cyclic amine III was converted to a borane complex of Compound I.

The active form of the catalyst in Step C is platinum black or palladium black, generated in situ from the corresponding oxides or halides by the amine boranes present in the reaction mixture.

The alcohol employed in Step C can be any aliphatic or alicyclic hydrocarbyl alcohol. In a preferred embodiment, the alcohol is a C$_{1-6}$ alkyl alcohol, such as methanol, ethanol, n-propanol, isopropanol, n-butanol, sec-butanol, and isobutanol. In a preferred aspect of this embodiment, the alcohol is methanol. The alcohol can be employed in any amount suitable for obtaining Compound I substantially free of any borane complex. The alcohol can suitably be employed in an amount of at least about 3 moles per mole of borane complex in the Step B product. The 3 moles of alcohol per mole of borane complex will insure complete conversion to the desired product (i.e., complete cleavage), resulting in a tri-alcholoxyborane by-product. The alcohol can be employed in Step C in an even larger excess and can in fact be employed as the reaction medium. Alternatively, an aprotic solvent can be employed as the Step C reaction medium. The aprotic solvents set forth above for use in Step A are also suitable for use in Step C.

Step C is suitably conducted at a temperature in the range of from about 0 to about 50° C., and is typically conducted at a temperature in the range of from about 10 to 40° C. (e.g., from about 15 to about 30° C.), and is more typically conducted at a temperature in the range of from about 15 to about 30° C. (e.g., from about 18 to about 25° C.).

The reaction time for Step C can vary widely depending upon, inter alia, the choice and relative amount of catalyst and alcohol employed and the choice of temperature. The reaction is nonetheless usually complete in about 24 hours or less, and is typically complete in about 8 hours or less (e.g., in from about 0.5 to about 6 hours).

A suitable procedure for conducting Step C is as follows: The Pt or Pd catalyst is added to the Step B reaction product dissolved (or dispersed or suspended) in an aprotic solvent, followed by addition of the alcohol. The reaction mixture is then aged at reaction temperature until cleavage of the borane complex is complete or substantially complete. Compound I can then be recovered (isolated) from the Step C reaction mixture by conventional means (e.g., filtration to remove the catalyst, thermal or vacuum removal of solvent, alcohol and alcoholoxyborate by-products, and so forth).

If desired, the progress of reaction steps A, B and/or C can be followed by monitoring the disappearance of a reactant (e.g., the disappearance of aldehyde III or amine III in Step A) and/or the appearance of the product (e.g., the appearance of iminium salt IV in Step A) using TLC, HPLC, NMR or GC.

An embodiment of the process of the present invention is a process for preparing Compound 1:

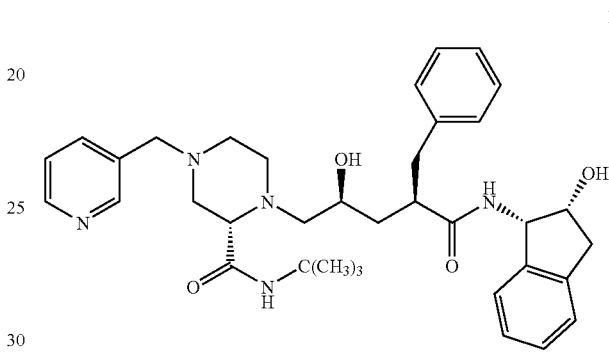

1 which comprises:

(A) reacting aldehyde 2:

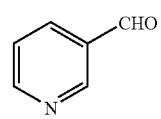

2 with piperazine 3:

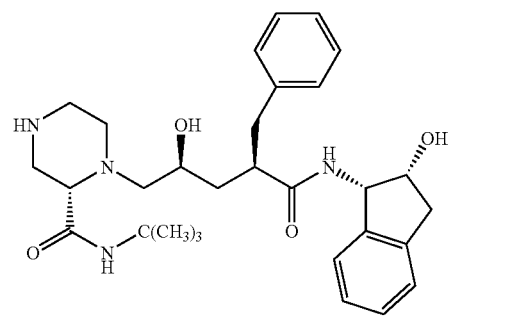

3 in an organic solvent and in the presence of a C$_{1-6}$ alkyl-carboxylic acid and with removal of by-product water, to form a reaction mixture comprising an iminium salt 4:

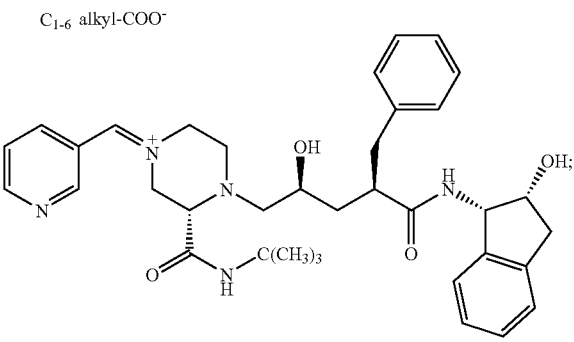

(B) adding a tetrahydroborate salt to the reaction mixture of Step A to obtain a product comprising Compound 1 and one or more borane complexes thereof; and (C) treating the product of Step B with a catalyst selected from the group consisting of Pt oxide, Pt halide, Pd oxide and Pd halide in the presence of a $C_{1-6}$ alkyl alcohol to cleave the one or more borane complexes and thereby obtain Compound 1 substantially free of any borane complex thereof.

Aspects of this embodiment include Step A as just described wherein:

(a-i) by-product water is removed from the reaction mixture of Step A by conducting Step A in the presence of a dehydrating agent (e.g., molecular sieves);

(a-ii) the solvent employed in Step A is an aprotic solvent (e.g., an ether such as THF);

(a-iii) Step A is conducted at a temperature in the range of from about 0 to about 30° C., or from about 10 to about 30° C. (e.g., from about 15 to about 28° C.), or from about 15 to about 25° C. (e.g., from about 18 to about 25° C.);

(a-iv) aldehyde 2 is employed in Step A in an amount in the range of from about 1 to about 2 moles per mole of piperazine 3, or from about 1.0 to about 1.5 moles (e.g., from about 1.0 to about 1.3 moles) of 2 per mole of 3;

(a-v) the $C_{1-6}$ alkylcarboxylic acid (e.g., acetic acid) is employed in Step A in an amount of from about 1 to about 2.5 equivalents (or from about 1.1 to about 2.0 equivalents, or from about 1.5 to about 2.0 equivalents) per equivalent of amino groups present in piperazine 3; and (a-vi) Step A includes the combination of any two or more of (a-i) to (a-v).

Other aspects of the preceding embodiment include Step A as originally described in the embodiment optionally including any one or more of the aspects (a-i) to (a-vi) above and Step B as originally described in the embodiment wherein:

(b-i) the tetrahydroborate salt added in Step B is an alkali metal salt or a quaternary ammonium salt of tetrahydroborate (e.g., $NaBH_4$);

(b-ii) the tetrahydroborate salt is added in Step B in an amount in the range of from about 0.8 to about 4 moles (or from about 0.8 to about 1.3 moles, or from about 1.0 to about 1.5 moles, or from about 1.0 to about 1.2 moles) per mole of piperazine 3;

(b-iii) Step B is conducted at a temperature in the range of from about 0 to about 30° C. (or from about 10 to about 30° C., or from about 15 to about 28° C., or from about 15 to about 25° C., or from about 18 to about 25° C.); and (b-iv) Step B includes any two or more of (b-i) to (b-iii).

Still other aspects of the preceding embodiment include Step A as originally described in the embodiment optionally including any one or more of the aspects (a-i) to (a-vi) above and Step B as originally described in the embodiment optionally including any one or more of the aspects (b-i) to (b-iv) above, and also include Step C as originally described in the embodiment wherein:

(c-i) the catalyst in Step C is employed in an amount in the range of from about 0.01 to about 0.20 moles (e.g., from about 0.05 to about 1.5 moles) per mole of piperazine 3;

(c-ii) the $C_{1-6}$ alkyl alcohol (e.g., methanol) in Step C is employed in an amount of at least about 3 moles per mole of borane complex in the Step B product;

(c-iii) Step C is conducted at a temperature in the range of from about 10 to about 40° C.; and (c-iv) Step C includes any two or more of (c-i) to (c-iii).

In this embodiment, the amount of alcohol employed in Step C can alternatively be expressed in units of volume (at 25° C. and atmospheric pressure) per unit weight. Specifically, the alcohol can be employed in an amount in the range of from about 2 to about 40 mL (e.g., from about 3 to about 6 mL) per gram of 3.

Another embodiment of the process of the present invention is a process for preparing Compound 1, which comprises:

(A) reacting aldehyde 2 with piperazine 3 in an aprotic solvent and in the presence of acetic acid and with removal of by-product water by conducting the reaction in the presence of a dehydrating agent, to form a reaction mixture comprising an iminium salt 4:

(B) adding Na tetrahydroborate to the reaction mixture of Step A to obtain a product comprising Compound 1 and one or more borane complexes thereof; and (C) treating the product of Step B with a catalytic amount of Pt oxide or Pt halide in the presence of methanol or ethanol to cleave the one or more borane complexes and thereby obtain Compound 1 substantially free of any borane complex thereof.

Aspects of this embodiment of the process include the process as just described incorporating any one or more of the following features:

(aa-i) the dehydrating agent in Step A comprises molecular sieves;

(aa-ii) the solvent employed in Step A is an ether (e.g., THF);

(aa-iii) Step A is conducted at a temperature in the range of from about 10 to about 30° C.;

(aa-iv) aldehyde 2 is employed in Step A in an amount in the range of from about 1.0 to about 1.5 moles per mole of piperazine 3;

(aa-v) acetic acid is employed in Step A in an amount in the range of from about 1.1 to about 2.0 equivalents per equivalent amino groups present in piperazine 3;

(bb-i) the Na tetrahydroborate is added in Step B in an amount in the range of from about 0.8 to about 1.3 moles per mole of piperazine 3;

(bb-ii) Step B is conducted at a temperature in the range of from about 10 to about 30° C.;

(cc-i) the catalyst in Step C is employed in an amount in the range of from about 0.05 to about 0.15 moles per mole of piperazine 3;

(cc-ii) the alcohol in Step C is methanol, employed in an amount in the range of at least about 3 moles per mole of borane complex in the Step B product; and (cc-iii) Step C is conducted at a temperature in the range of from about 15 to about 30° C.

Aldehyde 2 is available commercially from many sources. Alternatively, aldehyde 2 can be prepared by methods known in the art, such as those disclosed in *Ullmann's Encyclopedia of Industrial Chemistry*, Vol. A22, VCH, 1993, page 421 (and references cited therein), and as disclosed in U.S. Pat. No. 6,444,815. Piperazine 3 (also referred to in the art as indinavir penultimate) can be prepared as described in U.S. Pat. No. 5,646,148 (see Scheme II and Examples 4–6) and U.S. Pat. No. 5,618,937 (see Example 27).

The present invention also includes a process for preparing a compound of Formula (I) as heretofore described, which comprises (P) forming a reaction mixture by adding an aldehyde of Formula (II) as heretofore described, a cyclic amine compound of Formula (III) as heretofore described, and optionally a dehydrating agent to a composition comprising an admixture obtained by mixing a tetrahydroborate salt and a $C_{1-6}$ alkylcarboxylic acid in an organic solvent, wherein the carboxylic acid is employed in the admixture in an amount that is at least sufficient to neutralize each of the amino groups present in cyclic amine III and to acylate the tetrahydroborate to the extent that free borohydride is substantially absent from the reaction mixture; and (Q) aging the reaction mixture of Step P to form the compound of Formula (I) substantially free of any borane complex thereof.

All embodiments, aspects and features of Compound I, aldehyde II, cyclic amine III as set forth above with respect to the process comprising Steps A, B, and C are embodiments, aspects and features of this process as well. Alkylcarboxylic acids and solvents (e.g., aprotic solvents) as described above for use in Step A are suitable for use in Step P as well. The admixture in Step P can be a solution or slurry depending upon the choice of solvent. Alcohols (e.g., methanol) will typically form solutions, while ethers (e.g., THF) will typically result in slurries. Tetrahydroborate salts as described above for use in Step B are also suitable for use in Step P.

The process comprising Steps P and Q is related to, but different from the process comprising Steps A, B and C. In the P+Q process, the formation of a borane complex of Compound I is avoided, or at least minimized, by contacting the aldehyde II and piperazine III with a tetrahydroborate salt only after the tetrahydroborate salt is admixed with an alkylcarboxylic acid in an amount and under conditions sufficient to acylate the borohydride. It is the presence of free borohydride which results in the formation of a borane complex with the π deficient nitrogen in the $R^1$ group in Compound I. Accordingly, acylation of the borohydride to the extent that little or no free borohydride is present results in the formation of little or no borane complex in Step P. In contrast, the previous process involving Steps A, B and C permits formation of a borane complex of Compound I via Steps A and B, but then provides for the efficient cleavage of the complex in Step C.

The term "substantially absent" with respect to free borohydride in Step P means that all or nearly all of the borohydride mixed with the alkylcarboxylic acid to obtain the admixture is at least partially acylated by the alkylcarboxylic acid before the addition of aldehyde II and cyclic amine III. More particularly, the term means that less than about 10%, preferably less than 5%, and more preferably less than 1% of the molar amount of borohydride initially charged to the admixture exists as free (i.e., unacylated) borohydride in the admixture upon addition of aldehyde II and cyclic amine III. In the most preferred case, free borohydride cannot be detected in the admixture using conventional analytical means prior to addition of aldehyde II and cyclic amine III. The amount of free borohydride present in the admixture can be monitored and determined, for example, via IR, as described, for example, in *Lang's Handbook of Chemistry*, 15$^{th}$ edition, edited by J. A. Dean, (McGraw-Hill, New York, 1998), p. 7.61–62, 7.11.

The tetrahydroborate salt is typically employed in Step P in an amount which can achieve optimal conversion of cyclic amine III to Compound I. In one embodiment, the amount of the tetrahydroborate salt employed in Step P is in the range of from about 1 to about 2 moles per mole of cyclic amine III. In another embodiment, the tetrahydroborate salt is employed in an amount in the range of from about 1.2 to 1.5 moles (e.g., from about 1.2 to about 1.3 moles) per mole of cyclic amine III.

As already noted above, the $C_{1-6}$ alkylcarboxylic acid is employed in an amount that is at least sufficient to neutralize each of the amino groups present in cyclic amine III and to acylate the tetrahydroborate to the extent that free borohydride is substantially absent from the reaction mixture. In one embodiment, the $C_{1-6}$ alkylcarboxylic acid is employed in Step P in an amount of at least about 1 equivalent per each equivalent of amino groups present in cyclic amine III and in addition at least about 2 equivalents per equivalent of tetrahydroborate.

Aldehyde II is suitably employed in Step P in an amount that can achieve optional conversion of cyclic amine III to Compound I. In one embodiment, aldehyde II is employed in an amount in the range of from about 1 to about 2 moles per mole of cyclic amine III. In another embodiment, aldehyde II is employed in an amount in the range of from about 1.1 to 1.5 moles (e.g., from about 1.1 to about 1.3 moles) per mole of cyclic amine m.

Step P is suitably conducted at a temperature in the range of from about 0 to about 30° C., and is typically conducted at a temperature in the range of from about 10 to 30° C. (e.g., from about 15 to about 28° C.), and is more typically conducted at a temperature in the range of from about 15 to about 25° C. (e.g., from about 18 to about 25° C.).

The admixture employed in Step P is typically prepared by the addition of the borohydride to a solution of the alkylcarboxylic acid in the selected solvent. Because the reaction between the carboxylic acid and the borohydride is exothermic, slow addition of the borohydride and/or suitable temperature control is necessary to maintain the temperature of the admixture at or below about 30° C. Higher temperatures can result in self reduction of the acylborohydride. Upon completion of the borohydride addition, aldehyde II and cyclic amine III (optionally with additional solvent) are added to the admixture. This entire procedure is optionally but preferably conducted with agitation (e.g., stirring). The use of a dehydrating agent is optional but preferred. The dehydrating agent is suitably added to the admixture before addition of aldehyde II and cyclic amine III. If a dehydrating agent is not used, the amount of borohydride reducing agent must be increased to remove the by-product water, with a concomitant increase in the amount of alkylcarboxylic acid necessary for acylation. This approach requires more reagent and is thus more expensive. The dehydrating agents noted above as suitable for use in the A+B+C process are also suitable for use in this process. A preferred dehydrating agent is molecular sieves.

Once the reaction mixture is formed in Step P, it is aged in Step Q for a time and under conditions effective for achieving the desired degree of conversion of cyclic amine III to Compound I. Aging is typically conducted to achieve substantially complete conversion of cyclic amine III plus a high yield of Compound I. Step Q is suitably conducted at a temperature in the range of from about 5 to about 45° C., and is typically conducted at a temperature in the range of from about 15 to 35° C. (e.g., from about 15 to about 30).

The aging time in Step Q can vary widely depending upon (i) the choice and relative amounts of the reactants and reagents employed, the choice of temperature, and the level of conversion desired. The reaction is nonetheless usually complete in about 24 hours or less, and is typically complete in about 12 hours or less, and is often complete in about 6 hours or less (e.g., in from about 0.5 to about 5 hours).

Upon completion of aging Step Q, Compound I can be isolated using conventional recovery techniques. For example, the reaction mixture can be filtered to remove the dehydrating agent, quenched with an aqueous salt solution (e.g., brine), the pH adjusted to neutral or slightly basic (to convert the water soluble salt form of the product to the organically soluble free-base form), the filtrate separated into water and organic phases, and Compound I recovered from the organic phase by concentrating the phase by evaporative removal of a portion of the solvent, and then cooling the concentrated solution to precipitate Compound I.

An embodiment of the process of the invention comprising Steps P and Q is a process for preparing Compound 1, which comprises:

(P) forming a reaction mixture by adding aldehyde 2, piperazine 3, and optionally a dehydrating agent to a composition comprising an admixture obtained by mixing a tetrahydroborate salt and a $C_{1-6}$ alkylcarboxylic acid in an aprotic solvent, wherein the carboxylic acid is employed in the admixture in an amount that is at least sufficient to neutralize each of the amino groups present in piperazine 3 and to acylate the tetrahydroborate to the extent that free borohydride is substantially absent from the reaction mixture; and (Q) aging the reaction mixture of Step P to form Compound 1 substantially free of any borane complex thereof.

Aspects of this embodiment include Step P as just described wherein:

(p-i) the tetrahydroborate salt is Na tetrahydroborate;
(p-ii) the tetrahydroborate salt is employed in an amount in the range of from about 1 to about 2 moles per mole of piperazine 3;
(p-iii) the carboxylic acid is acetic acid;
(p-iv) the carboxylic acid is employed in an amount of at least about 1 equivalent per each equivalent of amino groups present in piperazine 3 and in addition at least about 2 equivalents per equivalent of tetrahydroborate;
(p-v) aldehyde 2 is employed in an amount of from about 1 to about 2 moles per mole of piperazine 3;
(p-vi) a dehydrating agent is present in the reaction mixture;
(p-vii) the optional dehydrating agent comprises molecular sieves;
(p-viii) Step P is conducted at a temperature in the range of from about 0 to about 30° C.; and
(p-ix) Step P includes the combination of any two or more of (p-i) to (p-viii).

Other aspects of the preceding embodiment include Step P as originally described in the embodiment optionally including any one or more of the aspects (p-i) to (p-ix) above and also include Step Q as originally described in the embodiment wherein Step Q is conducted at a temperature in the range of from about 5 to about 45° C.

Abbreviations used in the instant specification include the following:
AcOH=acetic acid
AIDS=acquired immunodeficiency syndrome
Bu=butyl
DMAC=N,N-dimethylacetamide
DME=1,2-dimethoxyethane
DMF=N,N-dimethylformamide
Et=ethyl
FTIR=fourier transform infrared spectroscopy
GC=gas chromatography
HIV=human immunodeficiency virus
HPLC=high performance liquid chromatography
LC-MS=liquid chromatography-mass spectroscopy
Me=methyl
MeOH=methanol
m.p.=melting point
MTBE=methyl tert-butyl ether
NMR=nuclear magnetic resonance
Ph=phenyl
Pr=propyl
THF=tetrahydrofuran
TLC=thin-layer chromatography
UV=ultraviolet The following examples serve only to illustrate the invention and its practice. The examples are not to be construed as limitations on the scope or spirit of the invention.

EXAMPLE 1

Preparation of Indinavir

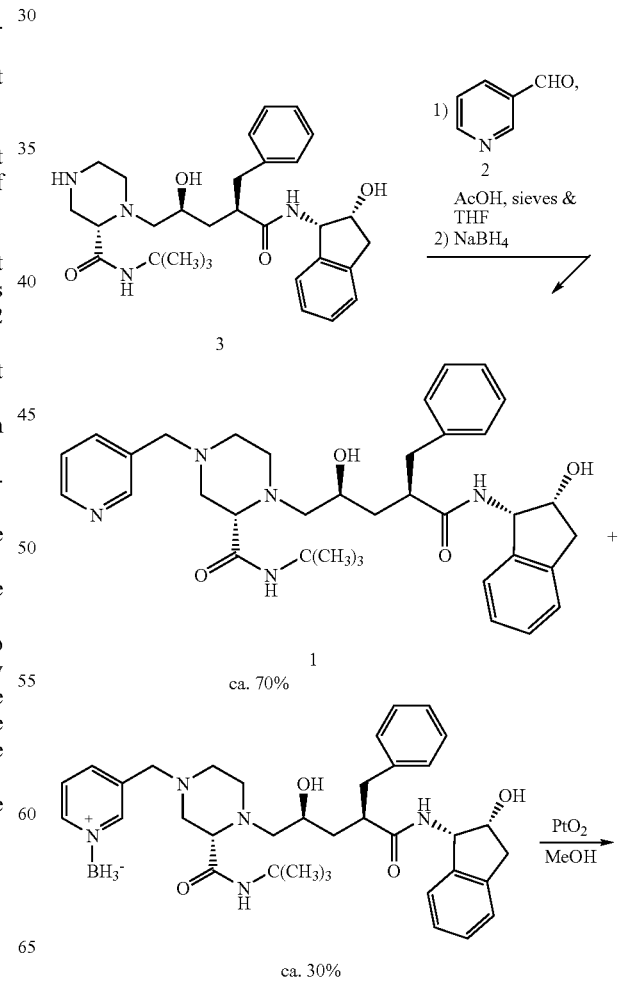

-continued

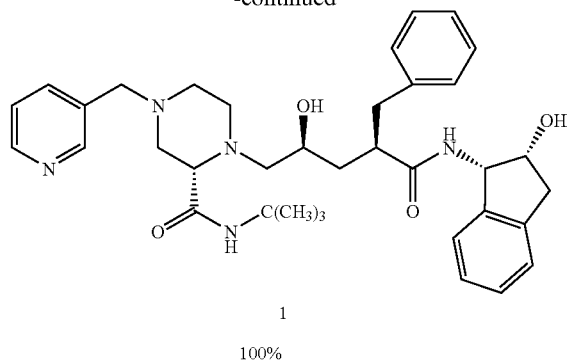

1
100%

Indinavir penultimate 3 (2.0 g, 3.82 mmol) was dissolved in 40 mL of dry THF, after which 3-pyridinecarboxaldehyde (2, 0.45 g, 4.2 mmol), acetic acid (1.4 mL 25 mmol) and 4 Å sieves (3 g) were added. The reaction mixture was aged at 20° C. for 30 minutes to preform the iminium salt intermediate. NaBH$_4$ (1.6 g, 4.2 mmol) was then added over a 30-minute period, maintaining the temperature at 20–25° C. The batch was then aged for three hours at 20° C. HPLC analysis indicated the conversion was >99% complete, with approximately 70% of the conversion to indinavir and approximately 30% to a pyridinyl-borane complex of indinavir. The sieves were removed by filtration and washed with 20 mL of THF. The filtrates were combined and the mixture quenched into brine. The pH of the quenched mixture was adjusted to a value of 8 with agitation, and then the aqueous layer was discarded.

PtO$_2$ (87 mg, 0.38 mmol) was added to the organic solution containing indinavir and its borane complex, whereupon the red-brown oxide immediately converted to very fine platinum black. Methanol (10 mL) was added and a mild evolution of hydrogen occurred over a period of about one hour. The batch was aged an additional two hours, whereupon HPLC analysis showed cleavage of the borane complex to be complete.

The batch was then concentrated to remove THF, methanol and trimethoxyborate, and the concentrated batch was then diluted with isopropyl acetate. The batch was heated to 70° C., saturated with water and allowed to slowly cool to 0–5° C. to promote crystallization. The product was removed by filtration and washed with isopropyl acetate. Yield of 1=2.16 g, 92% at a purity of 100% by HPLC.

$^1$H NMR (400 MHz, CDCl$_3$) δ 8.53 (dd J=1.6), 8.52 (d, J=2.0), 7.68 (bs), 7.60 (d, J=7.9, 2.0), 7.29 (m), 7.23 (m), 1.18–7.09 (m), 6.19 (d, J=8.5), 5.27 (dd, J=8.5, 4.8), 4.27 (m), 3.92 (br s), 3.81 (m), 3.49 (s), 3.12 (t, J=3.6), 3.02 (dd, J=16.7, 5.2), 2.98–2.47 (m), 2.34 (br s), 1.97, 1.56 (m), 1.50 (br s), 1.34 (s). $^{13}$C NMR (100 MHz, CDCl$_3$) δ 175.0, 169.4, 151, 149, 140.4, 140.3, 139.9, 137, 133, 129.1, 128.5, 127.9 126.7, 123.9, 126.5, 125.1 123.4, 73.0, 65.8, 64.1, 61.4, 60, 57.4, 54.6, 52.7, 51.1, 47.9, 46.5, 39.6, 39.1, 38.1, 29.0.

HPLC analyses were performed using an Inertsil ODS-2 25 cm×4.6 cm column (Metachem Technologies), 5 μm particle size, with the following parameters: temperature=25° C., UV detection at λ=220 nm, mobile phase=20% acetonitrile+80% 0.1% phosphate buffer, flow rate=1 mL/min, and injection volume=20 μL.

EXAMPLE 2

Preparation of 1-(phenyl)-4-((pyridin-3-yl)methyl)piperazine

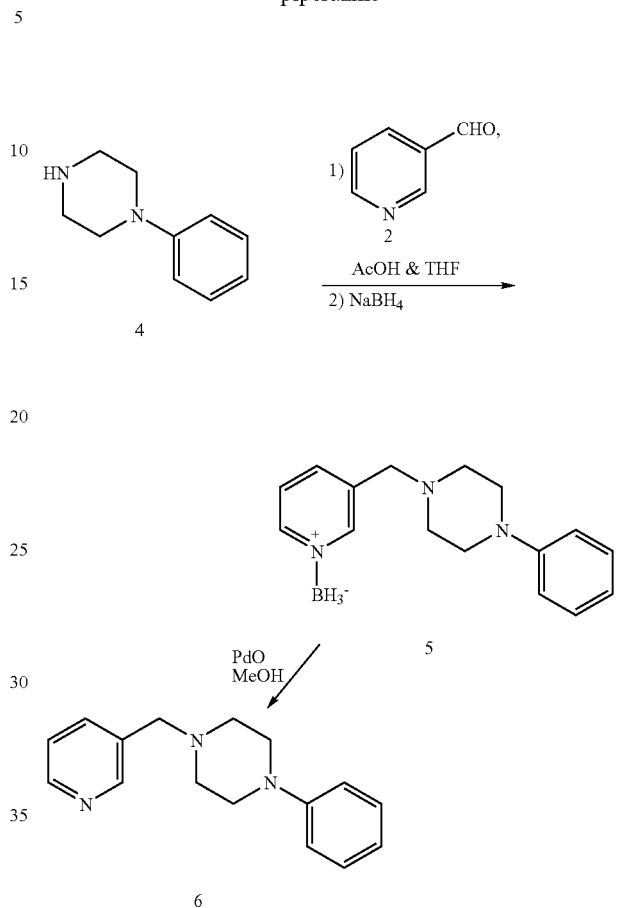

Step 1: Preparation of 3-((4-phenyl)piperazin-1-yl)methylpyridine-borane

1-Phenylpiperazine (4, 5.00 mL, 32.40 mmol, 1 equiv.), 3-pyridinecarboxaldehyde (2, 3.74 mL, 38.88 mmol, 1.2 equiv.), and acetic acid (glacial, 14.84 mL, 259.20 mmol, 8 equiv.) were dissolved in THF (anhydrous, 50 mL) and aged for 3 hours at 55° C. under a nitrogen blanket with stirring at 200 RPM. NaBH$_4$ (3.1270 g, 81.00 mmol, 8 equiv.) was then added slowly over 20 minutes to the reaction mixture. The reaction was 96.0% complete after 16 hours, as determined by monitoring 4 with HPLC. The reaction was then quenched with saturated NaHCO$_3$ (100 mL) and aged for 2 hours followed by the addition of brine (100 mL). The quenched reaction mixture was extracted with THF (100 mL×2), and the organic layer was dried first by rotavaporization and then in a vacuum oven at 45° C.

The TLC had R$_f$=0.31. The dried solid was purified with column chromatography. Purified compound 5 has a HPLC area 97.8% (m.p.=105–107° C.).

HPLC: t$_R$=6.598 min. $^1$H NMR (CDCl$_3$) δ: 2.60–2.62 (t, 7H), 3.18–3.20 (t, 4H), 3.60 (s, 2H), 6.86–6.88 (t, 1H), 6.91–6.93 (d, 2H), 7.24–7.28 (quar, 2H), 7.46–7.49 (quar, 1H), 7.95–7.97 (d, 1H), 8.49–8.50 (d, 1H), and 8.59 (s, 1H). $^{13}$C NNR (CDCl$_3$) δ: 49.3, 53.3, 59.6, 116.4, 120.2, 125.4, 129.4, 137.1, 139.7, 146.5, 147.9, and 150.0. LC-MS m/z: 267.3 (M$^+$).

HPLC analyses were performed using a Hewlett Packard 1050 HPLC system (Hewlett-Packard Co., Wilmington, Del.) with the following parameters: column=Zorbax C-8 (25 cm×4.6 mm), ambient temperature (about 20° C.), diode array detection at λ=202 nm, mobile phase=60% acetonitrile, 40% 5 mM $KH_2PO_4$/5 mM $K_2HPO_4$, flow rate=1 mL/min, injection volume=10 μL, and pressure=80 to 90 bar.

The $^1$H NMR of 5 set forth above provides evidence that the borane complex is with the pyridine nitrogen due to the chemical shift of the ring protons, particularly of the protons on the 4 and 5 positions of the heterocyclic ring.

The FTIR spectrum of 5 exhibited strong absorption due to B—H stretching in the range 2200 $cm^1$ to 2400 $cm^{-1}$, which is typical of amine borane complexes.

Step 2: Preparation of 1-(phenyl)-4-((pyridin-3-yl)methyl) piperazine 3-((4-phenyl)piperazin-1-yl)methylpyridine-borane 5 (200 mg, 0.749 mmol) was added to 20 mL of methanol at about 20° C. After complete dissolution, PdO (4.6 mg, 0.037 mmol) was added, and the reaction mixture aged for eight hours at 20–25° C. Palladium black was removed by filtration followed by vacuum concentration of the filtrate to remove methanol and trimethoxyborane. The resulting viscous oil was dissolved in hot hexanes and crystallized by slow cooling to 20° C. The product was washed with cold hexane and dried under vacuum. The yield of 6 was 97% with 100% purity, as determined by HPLC conducted using the system described in Example 1.

The $^1$H NMR of 6 is shown in Example 3. The $^1$H NMR of 6 differs from that of 5 primarily in the slight down-field chemical shift of the pyridine ring protons. Also, the absorbance at δ=2.61 for compound 5 includes the methylene group at the 3-position of the pyridine ring as well as the BH3 absorbance. By contrast the δ=2.61 for 6 represents only the methylene protons attached to the pyridine ring.

The FTIR spectrum of 6 did not contain a peak due to B—H stretching, demonstrating that the borane complex was completely cleaved.

EXAMPLE 3

Preparation of 1-(phenyl)-4-((pyridin-3-yl)methyl) piperazine

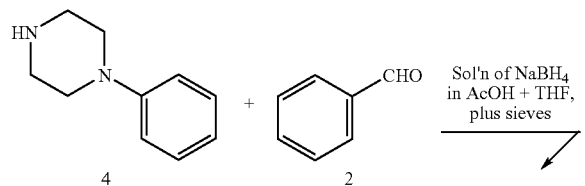

4      2

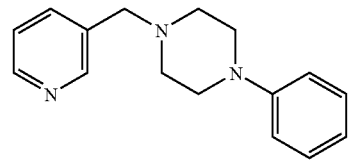

6

$NaBH_4$ (1.50 g, 38.88 mmol, 1.2 equiv.) was slowly added over 20 minutes to a solution of acetic acid (glacial, 11.13 mL, 194.41 mmol, 6 equiv.) in anhydrous THF (50 mL) at 20° C. under a nitrogen blanket with stirring at 200 RPM. After aging for another 20 minutes, pre-dried molecular sieves (3A, 45 g) and additional anhydrous THF (20 mL) were added to the reaction mixture and the stirring rate was increased to 350 RPM. Ten minutes after addition of the sieves, 1-phenylpiperazine (4, 5.00 mL, 32.40 mmol, 1 eq.) and 3-pyridinecarboxaldehyde (2, 3.74 mL, 38.88 mmol, 1.2 equiv.) were added, and the mixture aged for another 30 minutes, at which point the reaction was 100% complete, as determined by monitoring the disappearance of 4 with HPLC. The molecular sieves were removed by filtration. The filtrate containing the product was quenched into brine and the pH adjusted to 7.5 to 8. The organic layer containing the product was separated and the aqueous layer discarded. The organic layer was then concentrated to dryness and the solids dissolved in hot hexanes. The desired product was then crystallized by slow cooling to 5–10° C. The resulting crystals were vacuum filtered while cold and washed with cold hexane (50 mL×2). The product was then dried under vacuum at 45° C. and 75 mm Hg pressure. The isolated yield of compound 6 (HPLC area 99.3%, mp 70.5–72.0° C.) was 90.7%.

HPLC: $t_R$=7.434 min.

$^1$H NMR (400 MHz, $CDCl_3$) δ 2.59–2.61 (t, 4H), 3.17–3.20 (t, 4H), 3.56 (s, 2H), 6.83–6.87 (t, 1H), 6.90–6.93 (d, 2H), 7.23–7.28 (m, 3H), 7.68–7.71 (d, 1H), 8.50–8.52 (d, 1H), 8.57 (s, 1H). $^{13}$C NMR (100 MHz, $CDCl_3$) δ 49.3, 53.3, 60.4, 116.3, 120.0, 123.7, 129.4, 133.7, 137.1, 148.9, 150.6, 151.5. LC-MS m/z: 253.3 ($M^+$).

HPLC analyses were conducted using the same system and conditions as described in Example 2, Step 1.

The procedure employed in Example 2 for the preparation of Compound 6 (i.e., addition of $NaBH_4$ to a reaction mixture containing acetic acid, aldehyde 2 and piperazine 3) resulted in the formation of a pyridine-borane complex which necessitated a cleavage step to obtain Compound 6 free of borane complex. In contrast, the procedure employed in Example 3 (i.e., addition of aldehyde 2 and piperazine 3 to a $NaBH_4$-acetic acid solution) resulted in Compound 6 without formation of a pyridine-borane complex; i.e., a cleavage step was not necessary.

EXAMPLE 4

Preparation of 1-(phenyl)-4-((2-butyl-4-chloro-1H-imidazol-5-yl)methyl)piperazine

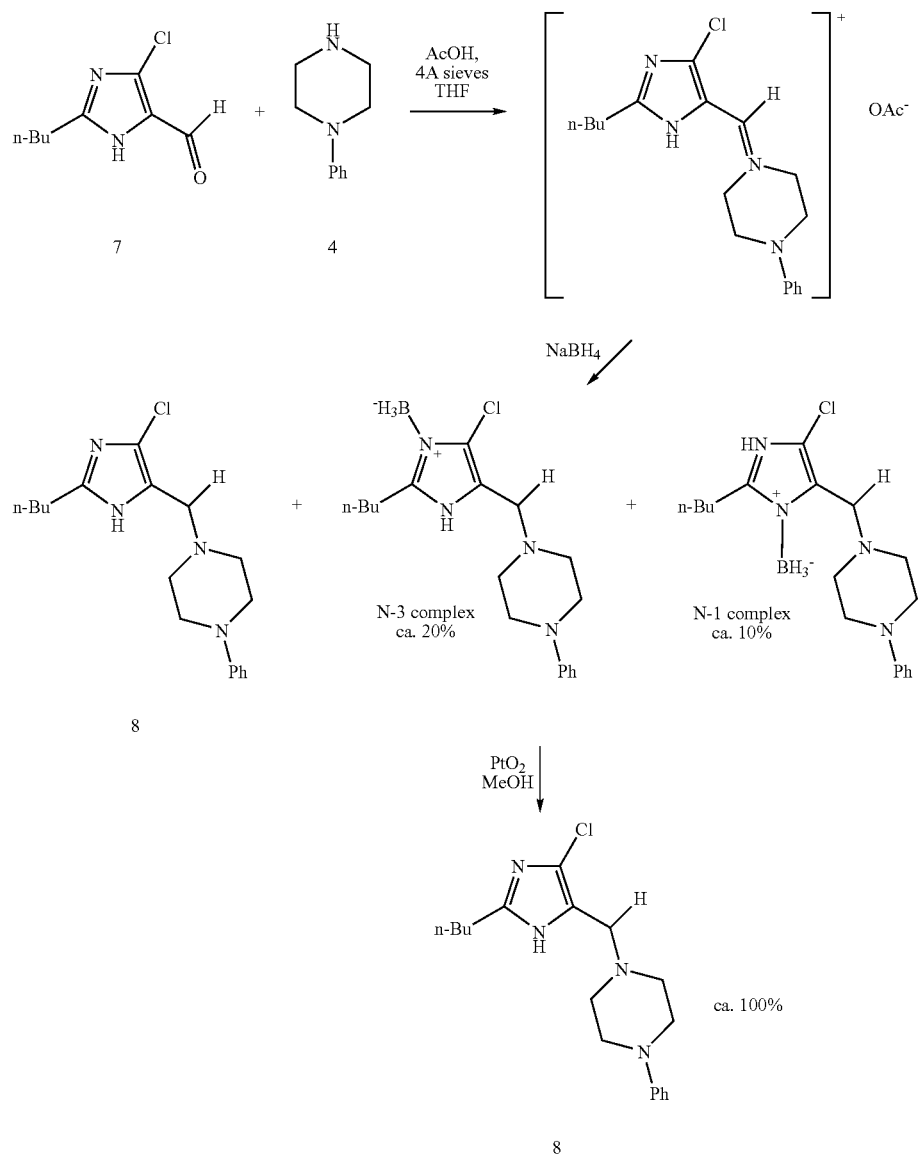

Anhydrous THF (25 mL), 2-butyl-4-chloro-1H-imidazole-5-carboxaldehyde (7, 2.00 g, 11 mmol), phenyl piperazine (4, 5.26 g, 32 mmol) and acetic acid (1 mL) were charged under a nitrogen blanket to a one-neck, 50 mL round bottomed flask equipped with a rubber septum and a magnetic stirring bar. The mixture was maintained at 20–25° C. with stirring for 2 hours, after which additional acetic acid (2.35 mL) was added, followed by 4 Å oven dried sieves (3 g). The reaction mixture was then aged for an additional hour. Sodium borohydride (0.39 g) was then added into the stirring mixture over about a 20 minute period, and the reaction mixture was aged overnight at 20° C. The reaction mixture was then filtered to remove the sieves and the filtered sieves then washed forward with THF (25 mL). Saturated NaHCO$_3$ (approximaely 10 mL) and saturated brine (approximaely 25 mL) were added to the filtrate, and the mixture was stirred for about 15 minutes, after which the pH of the solution was adjusted to 8 using a 25% solution of NaOH and allowed to sit for 30 minutes. The organic layer, containing the product 8 and borane complexes thereof, was separated and concentrated in vacuo to an off-white solid. The residue was dissolved in methanol (25 mL). The product mixture was determined by HPLC to contain approximately 55+% uncomplexed 8, about 20% N-3 borane complex, and about 10% N-1 borane complex. The product additionally contained some residual starting aldehyde 7, about 5% piperazine-borane complex, and several low-level impurities. It is noted that only the imidazole-borane complexes are stable to acid, and thus, if the crude product had been quenched in brine (versus quenching with bicarbonate and brine), followed by adjusting the pH to 7.0–8.0, the product mixture would have contained no piperazine-borane complex.

Platinum (II) oxide (0.1 mmol) was added to the above solution and the mixture was allowed to stir overnight. Activated carbon was then added and the mixture aged another hour. The catalyst was then removed by filtration through a Whatman glass microfiber filter (934-AH) precoated with Celite, followed by a methanol flush (approximaely 15 mL). Crystallization of the product 8 was then effected through the dropwise addition of distilled water (about 6 mL) over a period of one hour. The white, crystalline product was isolated by filtration, washed with water (about 25 mL) and dried under vacuum at 40° C. over a twelve hour period. Yield was 3.01 g (90%) with an HPLC purity of 98%. The isolated product was free of borane complex.

$^1$H NMR (400 MHz, CDCl$_3$) δ 10.07 (s, 1H), 7.31–7.21 (m, 2H), 6.91–6.85 (m, 3H), 3.53 (s, 2H), 3.17–3.15 (m, 4H), 2.67–2.61 (m, 6H), 1.67 (sept, J=7.6 Hz, 2H), 1.36 (sept, J=7.6 Hz, 2H), 0.90 (t, J=7.6 Hz, 3H); $^{13}$C NMR (100 MHz, CDCl$_3$) δ 150.98, 147.37, 129.08, 119.83, 115.99, 52.74, 51.05, 48.90, 30.23, 28.44, 22.25, 13.70; IR (neat) 2929.0, 2868.9, 2814.3, 2765.7, 1598.7, 1503.6, 1450.0, 1421.5, 1386.9, 1370.7, 1347.0, 1329.7, 1300.0, 1276.7, 1146.3, 1104.4, 1082.6, 1035.7, 1007.5, 947.1, 924.2, 880.49, 804.9, 755.7, 735.1, 690.3 cm$^{-1}$ HRMS (ESI, M+1) calc'd for $C_{18}H_{25}ClN_4$ 332.90. found 333.2.

HPLC analyses were performed using an Inertsil ODS-2 25 cm×4.6 cm column (Metachem Technologies), 5 μm particle size, with the following parameters: temperature=25° C.); UV detection at λ=220 nm; mobile phases=20% acetonitrile (A)+80% 0.1% phosphate buffer (B) for 14 minutes, then 90% A+10% B for 11 minutes, then 20% A+80% B for 5 minutes; flow rate=1.5 mL/min; and injection volume=20 μL.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A process for preparing a compound of Formula (I):

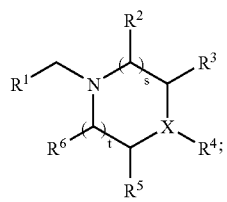

which comprises:
(A) reacting an aldehyde of Formula (II):

R$^1$—CHO    (II)

with a cyclic amine compound of Formula (III):

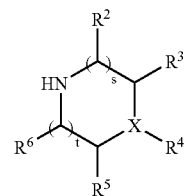

in an organic solvent and in the presence of a $C_{1-6}$ alkyl-carboxylic acid and with removal of by-product water, to form a reaction mixture comprising an iminium salt of Formula (IV):

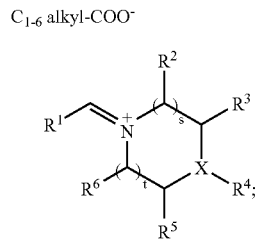

(B) adding a tetrahydroborate salt to the reaction mixture of Step A to obtain a product comprising a compound of Formula (I) and one or more borane complexes thereof; and (C) treating the product of Step B with a catalyst selected from the group consisting of Pt oxide, Pt halide, Pd oxide and Pd halide in the presence of an alcohol to cleave the one or more borane complexes and thereby obtain the compound of Formula (I) substantially free of any borane complex thereof;

wherein:

X is CH or N;

R$^1$ is a heteroaryl which is (I) a 5- or 6-membered heteroaromatic ring or (ii) a 9- or 10-membered fused, bicyclic ring system in which both rings are aromatic rings and at least one of the rings is a heteroaromatic ring; wherein the heteroaryl contains at least one carbon atom, one or more nitrogen atoms, optionally one or more O atoms, and optionally one or more S atoms; wherein at least one ring nitrogen in the heteroaryl has an unbonded electron pair that is not utilized in the aromatic π system of the heteroaryl; and wherein the heteroaryl is optionally substituted with from 1 to 5 substituents each of which is independently:

(1) halo,
(2) —C$_{1-6}$ alkyl,
(3) —C$_{1-6}$ alkyl mono-substituted with —OH, —O—C$_{1-6}$ alkyl, —CO$_2$R$^a$, —S(=O)R$^c$, or —SO$_2$R$^c$,
(4) —O—C$_{1-6}$ alkyl,
(5) —O—C$_{1-6}$ alkyl mono-substituted with —OH, —O—C$_{1-6}$ alkyl, —CO$_2$R$^a$, —S(=O)R$^c$, or —SO$_2$R$^c$,
(6) —OH,
(7) —CO$_2$R$^a$,
(8) —C(=O)N(R$^a$R$^b$),
(9) —S(=O)R$^c$,
(10) —SO$_2$R$^c$,

(11) aryl, optionally substituted with from 1 to 5 substituents each of which is independently halo, —OH, —$C_{1-6}$ alkyl, —O—$C_{1-6}$ alkyl, —$CO_2R^a$, —S(=O)$R^c$, or —$SO_2R^c$,
(12) —$C_{1-6}$ alkyl-aryl, wherein the aryl is optionally substituted with from 1 to 5 substituents each of which is independently halo, —OH, —$C_{1-6}$ alkyl, —O—$C_{1-6}$ alkyl, —$CO_2R^a$, —S(=O)$R^c$, or —$SO_2R^c$,
(13) HetA, or
(14) —$C_{1-6}$ alkyl-HetA;
each of $R^2$, $R^3$, $R^5$ and $R^6$ is independently:
(1) —H,
(2) —$C_{1-6}$ alkyl,
(3) —$C_{1-6}$ alkyl mono-substituted with —OH, —O—$C_{1-6}$ alkyl, —$CO_2R^a$, —S(=O)$R^c$, or —$SO_2R^c$,
(4) —O—$C_{1-6}$ alkyl,
(5) —O—$C_{1-6}$ alkyl mono-substituted with —OH, —O—$C_{1-6}$ alkyl, —$CO_{02}R^a$, —S(=O)$R^c$, or —$SO_2R^c$,
(6) —OH,
(7) —$CO_{02}R^a$,
(8) —CO(=O)N($R^aR^d$),
(9) —S(=O)$R^c$,
(10) —$SO_2R^c$,
(11) aryl, optionally substituted with from 1 to 5 substituents each of which is independently halo, —OH, —$C_{1-6}$ alkyl, —O—$C_{1-6}$ alkyl, —$CO_2R^a$, —S(=O)$R^c$, or —$SO_2R^c$,
(12) —$C_{1-6}$ alkyl-aryl, wherein the aryl is optionally substituted with from 1 to 5 substituents each of which is independently halo, —OH, —$C_{1-6}$ alkyl, —O—$C_{1-6}$ alkyl, —$CO_2R^a$, —S(=O)$R^c$, or —$SO_2R^c$,
(13) HetA, or
(14) —$C_{1-6}$ alkyl-HetA;
$R^4$ is:
(1) —H,
(2) —$C_{1-20}$ alkyl, which is:
 (a) optionally substituted with from 1 to 7 substituents each of which is independently:
  (i) —OH,
  (ii) —$C_{1-6}$ alkyl,
  (iii) —O—$C_{1-6}$ alkyl,
  (iv) —$CO_2R^a$,
  (v) —C(=O)N($R^aR^b$),
  (vi) —S(=O)$R^c$, or
  (vii) —$SO_2R^c$, and
 (b) optionally substituted with from 1 to 3 substituents each of which is independently:
  (i) —$R^k$,
  (ii) —$C_{1-6}$ alkyl-$R^k$,
  (iii) —C(=O)—$R^k$, or
  (iv) —C(=O)N($R^a$)$R^k$, or
(3) —$R^k$;
each $R^a$ and $R^b$ is independently —H or —$C_{1-6}$ alkyl;
each $R^c$ is independently —$C_{1-6}$ alkyl;
each $R^d$ is independently —H, —$C_{1-6}$ alkyl or —$C_{1-6}$ haloalkyl;
each $R^k$ is independently an optionally substituted carbocycle or an optionally substituted heterocycle;
carbocycle in $R^k$ is independently (i) a $C_3$ to $C_8$ monocyclic, saturated or unsaturated ring, (ii) a $C_7$ to $C_{12}$ bicyclic ring system, or (iii) a $C_{11}$ to $C_{16}$ tricyclic ring system, wherein each ring in (ii) or (iii) is independent of, fused to, or bridged with the other ring or rings and each ring is saturated or unsaturated; wherein the carbocycle is optionally substituted with from 1 to 7 substituents each of which is independently
(1) halogen, provided that the ring of the carbocycle substituted with the halogen is aromatic,
(2) —OH,
(3) —$C_{1-6}$ alkyl, optionally mono-substituted with —OH, —O—$C_{1-6}$ alkyl, —CN, —$NO_2$, —C(=O)N($R^aR^b$), —$CO_2R^a$, —S(=O)$R^c$, —$SO_2R^c$, —$SO_2$N($R^aR^b$), —N($R^a$)$SO_2R^c$, —$C_{3-8}$ cycloalkyl, phenyl, —O-phenyl, or HetB,
(4) —$C_{2-6}$ alkenyl,
(5) —$C_{2-6}$ alkynyl,
(6) —O—$C_{1-6}$ alkyl,
(7) —CN,
(8) —$NO_2$,
(9) —C(=O)N($R^aR^b$),
(10) —$CO_2R^a$,
(11) —S(=O)$R^c$,
(12) —$SO_2R^c$,
(13) —N($R^a$)$SO_2R^c$,
(14) —$SO_2$N($R^aR^b$),
(15) —$C_{3-8}$ cycloalkyl,
(16) phenyl,
(17) —O-phenyl, or
(18) HetB;
heterocycle in $R^k$ is independently (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to the other ring or rings and each ring is saturated or unsaturated; wherein the monocyclic ring, bicyclic ring system, or tricyclic ring system contains from 1 to 6 heteroatoms independently selected from N, O and S; wherein any one or more of the nitrogen and sulfur heteroatoms is optionally oxidized, and any one or more of the nitrogen heteroatoms is optionally quaternized; and wherein the heterocycle is optionally substituted with from 1 to 7 substituents each of which is independently
(1) halogen, provided that the ring of the heterocycle substituted with the halogen is aromatic,
(2) —OH,
(3) —$C_{1-6}$ alkyl, optionally mono-substituted with —OH, —O—$C_{1-6}$ alkyl, —CN, —$NO_2$, —C(=O)N($R^aR^b$), —$CO_2R^a$, —S(=O)$R^c$, —$SO_2R^c$, —$SO_2$N($R^aR^b$), —N($R^a$)$SO_2R^c$, —$C_{3-8}$ cycloalkyl, phenyl, —O-phenyl, or HetB,
(4) —$C_{2-6}$ alkenyl,
(5) —$C_{2-6}$ alkynyl,
(6) —O—$C_{1-6}$ alkyl,
(7) —CN,
(8) —$NO_2$,
(9) —C(=O)N($R^aR^b$),
(10) —$CO_2R^a$,
(11) —S(=O)$R^c$,
(12) —$SO_2R^c$,
(13) —N($R^a$)$SO_2R^c$,
(14) —$SO_2$N($R^aR^b$),
(15) —$C_{3-8}$ cycloalkyl,
(16) phenyl,
(17) —O-phenyl, or
(18) HetB;
 and with the proviso that (a) when a ring nitrogen is part of a non-aromatic ring in $R^k$, the nitrogen is a tertiary amine or is quatemized and (b) when a ring sulfur is part of a non-aromatic ring and is attached to ring carbons in $R^k$, the sulfur is a sulfoxide (—S(=O)—) or a sulfone (—S($O_2$)—);

each HetA is independently a 5- or 6-membered heteroaromatic ring containing from 1 to 3 heteroatoms independently selected from O and S, wherein the heteroaromatic ring is optionally fused with a benzene ring; wherein the optionally fused heteroaromatic ring is optionally substituted with from 1 to 4 substituents each of which is independently halo, —$C_{1-6}$ alkyl, or —O—$C_{1-6}$ alkyl;

each HetB is independently a 5- or 6-membered saturated or unsaturated heterocyclic ring containing from 1 to 4 heteroatoms independently selected from N, O and optionally oxidized S, wherein the heterocyclic ring is optionally fused with a benzene ring; and wherein the optionally fused heterocyclic ring is optionally substituted with from 1 to 7 substituents each of which is independently halogen, provided that the ring to which the halogen is attached is aromatic, —$C_{1-6}$ alkyl, —O—$C_{1-6}$ alkyl, or —$CO_2R^a$; and with the proviso that when HetB is not aromatic, then any ring nitrogen is a tertiary amino nitrogen and any ring sulfur that is attached to ring carbons is a sulfoxide or a sulfone; and s and t are each an integer equal to zero or 1, with the proviso that s+t=1 or 2.

2. The process according to claim 1, wherein by-product water is removed from the reaction mixture of Step A by conducting Step A in the presence of a dehydrating agent.

3. The process according to claim 1, wherein the solvent employed in Step A is an aprotic solvent.

4. The process according to claim 1, wherein Step A is conducted at a temperature in the range of from about 0 to about 30° C.

5. The process according to claim 1, wherein aldehyde II is employed in Step A in an amount in the range of from about 1 to about 5 moles per mole of cyclic amine III.

6. The process according to claim 1, wherein the $C_{1-6}$ alkylcarboxylic acid is employed in Step A in an amount in the range of from about 1 to about 3 equivalents per equivalent of amino groups present in cyclic amine III.

7. The process according to claim 1, wherein the tetrahydroborate salt added in Step B is an alkali metal salt or a quaternary ammonium salt of tetrahydroborate.

8. The process according to claim 1, wherein the tetrahydroborate salt is added in Step B in an amount in the range of from about 0.8 to about 5 moles per mole of cyclic amine III.

9. The process according to claim 1, wherein Step B is conducted at a temperature in the range of from about 0 to about 30° C.

10. The process according to claim 1, wherein the catalyst in Step C is employed in an amount in the range of from about 0.01 to about 0.2 moles per mole of cyclic amine III.

11. The process according to claim 1, wherein the alcohol employed in Step C is a $C_{1-6}$ alkyl alcohol.

12. The process according to claim 1, wherein the alcohol employed in Step C is employed in an amount of at least about 3 moles per mole of borane complex in the Step B product.

13. The process according to claim 1, wherein Step C is conducted at a temperature in the range of from about 0 to about 50° C.

14. A process according to claim 1, wherein the compound of Formula (I) is Compound 1:

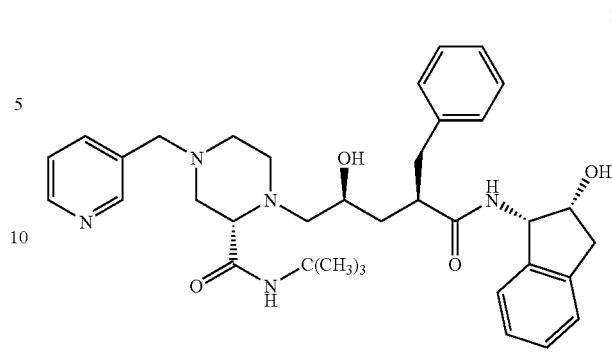

which comprises:

(A) reacting an aldehyde of Formula (II) which is aldehyde 2:

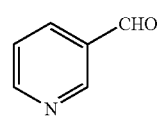

with a cyclic amine of Formula (III) which is piperazine 3:

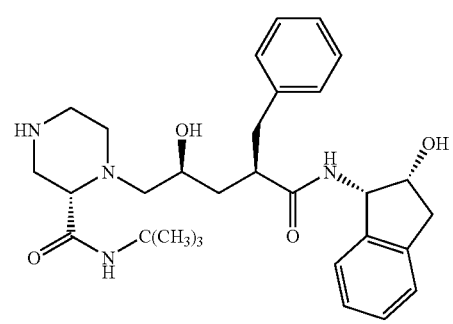

in an organic solvent and in the presence of a $C_{1-6}$ alkylcarboxylic acid and with removal of by-product water, to form a reaction mixture comprising an iminium salt of Formula (IV) which is iminium salt 4:

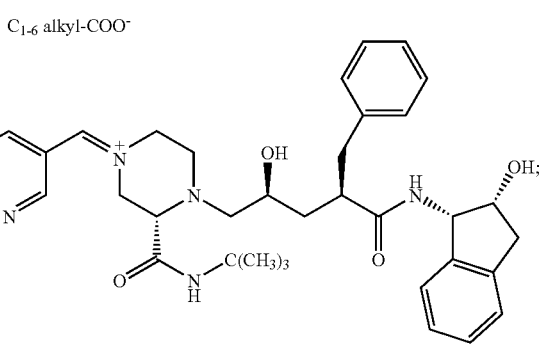

(B) adding a tetrahydroborate salt to the reaction mixture of Step A to obtain a product comprising Compound 1 and one or more borane complexes thereof; and (C) treating the product of Step B with a catalyst selected from the group consisting of Pt oxide, Pt halide, Pd oxide and Pd halide in the presence of a $C_{1-6}$ alkyl alcohol to cleave the one or more borane complexes and thereby obtain Compound 1 substantially free of any borane complex thereof.

15. The process according to claim 14, wherein:

by-product water is removed from the reaction mixture of Step A by conducting Step A in the presence of a dehydrating agent;

the solvent employed in Step A is an aprotic solvent;

Step A is conducted at a temperature in the range of from about 0 to about 30° C.;

aldehyde 2 is employed in Step A in an amount of from about 1 to about 2 moles per mole of piperazine 3; and the $C_{1-6}$ alkylcarboxylic acid is employed in Step A in an amount of from about 1 to about 2.5 equivalents per equivalent of amino groups present in piperazine 3.

16. The process according to claim 15, wherein the tetrahydroborate salt added in Step B is an alkali metal salt or a quaternary ammonium salt of tetrahydroborate;

the tetrahydroborate salt is added in Step B in an amount in the range of from about 0.8 to about 4 moles per mole of piperazine 3; and Step B is conducted at a temperature in the range of from about 0 to about 30° C.

17. The process according to claim 16, wherein the catalyst in Step C is employed in an amount in the range of from about 0.01 to about 0.20 moles per mole of piperazine 3;

the $C_{1-6}$ alkyl alcohol in Step C is employed in an amount of at least about 3 moles per mole of borane complex in the Step B product; and Step C is conducted at a temperature in the range of from about 10 to about 40° C.

18. The process according to claim 14, wherein by-product water is removed from the reaction mixture of Step A by conducting Step A in the presence of a dehydrating agent comprising molecular sieves;

the solvent employed in Step A is an ether;

Step A is conducted at a temperature in the range of from about 10 to about 30° C;

aldehyde 2 is employed in Step A in an amount of from about 1.0 to about 1.5 moles per mole of piperazine 3;

the $C_{1-6}$ alkylcarboxylic acid is acetic acid employed in Step A in an amount of from about 1.1 to about 2.0 equivalents per equivalent amino groups present in piperazine 3;

the tetrahydroborate salt added in Step B is Na tetrahydroborate added in an amount in the range of from about 0.8 to about 1.3 moles per mole of piperazine 3;

Step B is conducted at a temperature in the range of from about 10 to about 30° C.;

the catalyst in Step C is Pt oxide or Pt halide, employed in an amount in the range of from about 0.05 to about 0.15 moles per mole of piperazine 3;

the $C_{1-6}$ alkyl alcohol in Step C is methanol or ethanol, employed in an amount in the range of at least about 3 moles per mole of borane complex in the Step B product; and Step C is conducted at a temperature in the range of from about 15 to about 30° C.

* * * * *